(12) United States Patent
Thompson et al.

(10) Patent No.: US 6,664,086 B2
(45) Date of Patent: Dec. 16, 2003

(54) CDNA, GENOMIC, AND PREDICTED PROTEIN SEQUENCES OF LEARNING-INDUCED KINASES

(75) Inventors: Richard F. Thompson, Corona del Mar, CA (US); Hirishi Gomi, Asaha (JP); William Sun, San Diego, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 10/174,794

(22) Filed: Jun. 18, 2002

(65) Prior Publication Data

US 2003/0166220 A1 Sep. 4, 2003

Related U.S. Application Data

(62) Division of application No. 09/411,628, filed on Oct. 1, 1999, now Pat. No. 6,428,994.
(60) Provisional application No. 60/102,906, filed on Oct. 2, 1998.
(51) Int. Cl.[7] .................................................. C12N 9/12
(52) U.S. Cl. ........................................ 435/194; 530/350
(58) Field of Search ........................ 435/194; 530/350; 514/2

(56) References Cited

PUBLICATIONS

Taglienti et al., "Molecular Cloning of the Epidermal Growth Factor—Stimulated Protein Kinase P56 Kkiamre" Oncogene, vol. 13, No. 12, pp. 2563–2574, Dec. 19, 1996.*

* cited by examiner

*Primary Examiner*—Laurie Scheiner
(74) *Attorney, Agent, or Firm*—Bingham McCutchen LLP; David W. Maher

(57) ABSTRACT

To elucidate molecular mechanisms in learning and memory, the expression of mRNAs in brains of rabbitsundergoing eyeblink conditioning was analyzed. Infusion of the transcription inhibitor actinomycin D (ActD) into the cerebellar nuclei reversibly blocked learning but not performance of the CR. Differential display PCR (DD-PCR) analysis of cerebellar RNAs from trained and pseudo-trained rabbits identified a 207-bp band that was induced with learning. The fragment was used to isolate a cDNA from a λgt11 rabbit brain library containing a 1698-bp open-reading frame. The genomic sequence also has been obtained and is reported. The deduced amino acid sequence contains the KKIAMRE motif, which is conserved among cdc2-related kinases. These results suggest that there is a new category of cdc2-related kinases in the brain whose function may be important in learning and memory.

13 Claims, 13 Drawing Sheets

```
                                                     SEQ ID NO: 3                      CGGCC           -248
CTGCGAGGTGCCGAGCTTGGGCCCGGGGAGGCGGGGGCTCGGCCTCCCCTGCTTCCCCCGGGGGCCGGGACTGCCGTCGG       -162
CGGGGTCTCTGTCGCGCGGCCTGGGGCTGCTGGTGTGCAGGCGTCTTCTAGACCTGCGAGCGACATGCATTTCGCCTC         -81
CGGGGTCTGTCGCGCGGCCTGGGGCTGCTGGTGTGCAGGCGTCTTCTAGACCTGCGAGCGACATGCATTTCGCCTC            0
ATGGAAAAATATGAGAACCTTGGATTGGTTGGAGAAGGGAGTTATGGAAGTGTAGGAATAAAGATAGTGGA                 81
 M  E  K  Y  E  N  L  G  L  V  G  E  G  S  Y  G  M  V  M  K  C  R  N  K  D  S  G       27
SEQ ID NO: 4
AGAATTGTGGCCATCAAGAAGTTCCTAGAAAGTGATGATGACAAAAATGGTTAAAAAAATTGCTATGCGAGAAATCAAGTTA    162
 R  I  V  A  I  K  K  F  L  E  S  D  D  D  K  M  V  K  K  I  A  M  R  E  I  K  L       54
CTAAAGCAACTGAGGCATGAAAATTGGTGAATCTGTTGGAGTGTGTAAAAAAAACGATGGTACCTAGTCTTTGAA            243
 L  K  Q  L  R  H  E  N  L  V  N  L  L  E  V  C  K  K  K  R  W  Y  L  V  F  E          81
TTTGTTGACCACGATTCTTGATGACTTGGAACTCTTTCCAAATGGACTAGATGACCAAGTAGTTCAAAGTATTTGTTT        324
 F  V  D  H  T  I  L  D  D  L  E  L  F  P  N  G  L  D  D  Q  V  V  Q  K  Y  L  F      108
CAGATTATTAATGGAATTGGATTTTGTCACAGTCACAATATCATACATAGAGATATAAAGCCAGAGAATATATTGGTCTCC     405
 Q  I  I  N  G  I  G  F  C  H  S  H  N  I  I  H  R  D  I  K  P  E  N  I  L  V  S      135
CAGTCTGGCGTTGTCAAGTTATGTGATTTTGGATTTGCACGGACACTGGCAGCTCCCGGAGAGGTTACACTGATTATGTG      486
 Q  S  G  V  V  K  L  C  D  F  G  F  A  R  T  L  A  A  P  G  E  V  Y  T  D  Y  V      162
GCAACTCGATGGTACAGAGCTCCAGAACTACTGGTTGGTGATGTCAAGTATGGCAAAGCTGTGTGGATGTGTGGCCATTGGT    567
 A  T  R  W  Y  R  A  P  E  L  L  V  G  D  V  K  Y  G  K  A  V  D  V  W  A  I  G      189
TGTCTGGTAACTGAAATGCTCATGGGGGAACCCCTGTTCCTGGAGACTTGATATTGATCAGTTTATCTTATTATGAGG        648
 C  L  V  T  E  M  L  M  G  E  P  L  F  P  G  D  S  D  I  D  Q  L  Y  L  I  M  R      216
```

FIG. 4A.

```
TGTTTAGGTAATCTAATTCCAAGACACCAGGAGCTTTTTATAAAAATCCTGTGTTGCTGGAGTAAGGTTGCCTGAAATC    729
 C  L  G  N  L  I  P  R  H  Q  E  L  F  Y  K  N  P  V  F  A  G  V  R  L  P  E  I    243

AAGGAATCAGAACCTCTTGAAAGACGCTATCCCAAGCTCTCAGAAGTTGTGATAGATTTAGCAAAGAAATGCTTACATGTT    810
 K  E  S  E  P  L  E  R  R  Y  P  K  L  S  E  V  V  I  D  L  A  K  K  C  L  H  V    270

GACCCAGACAAAAGGCCCTTCTGTGTGCTGAGCTCTTCAGATGGATTGCTGAGCGGTTTCT                       891
 D  P  D  K  R  P  F  C  A  E  L  L  H  H  D  F  F  Q  M  D  G  F  A  E  R  F  S    297

CAGGAACTACAGATGAAAGTACAGAGATGCCAGAGAAATCCCAGAACAGAAAGAAGAAAG                        972
 Q  E  L  Q  M  K  V  Q  K  D  A  R  N  I  S  L  K  K  S  Q  N  R  K  K  E  K       324

GAAAAGGATGATTCCTTAGGCGAAGAAAGAAAAACACTAGTGGTACAGGATACCAATGTTGACTCCAAATTTAAGGATTCT  1053
 E  K  D  D  S  L  G  E  E  R  K  T  L  V  V  Q  D  T  N  V  D  S  K  F  K  D  S    351

AAAGTATTTAAAATAAAAGGATCAAAAATTGATGGAGAAAAGTTGACAAAGGCAATAGAGCAGCTGTCTCCATGACAGTG   1134
 K  V  F  K  I  K  G  S  K  I  D  G  E  K  V  D  K  G  N  R  A  A  V  S  M  T  V    378

GGACCAAGCCACATCAAAGCAGTGCCTTCCACAAGCCTGCAGAGACTGCAGCAATGTCAGTGTGGATCACACAAGGAATCCA 1215
 G  P  S  H  I  K  A  V  P  S  T  S  L  R  D  C  S  N  V  S  V  D  H  T  R  N  P    405

GGCATGGCCATTCCCCGCCTTACGCACAATCTTTCTGCAGTTGTATTCCATTGTTAAGCCAAATAACATTCTCCATCAGGA 1296
 G  M  A  I  P  R  L  T  H  N  L  S  A  V  A  P  G  I  N  S  G  M  G  T  I  P  G    432

GTTCAGAGTTACAGAGTGGATGAGAAGACTAAGAAGTATTGTATTCCATTGTTAAGCCAAATAACATTCTCCATCAGGC   1377
 V  Q  S  Y  R  V  D  E  K  T  K  K  Y  C  I  P  F  V  K  P  N  K  H  S  P  S  G    459

ATTTATAATATGAATGTGACCACATCAGTCTCCAGTGAAAAGAACCTCCTTCAGGCAAACAAGAAAAGAGGGAGTACTCC  1458
 I  Y  N  M  V  T  T  S  V  S  S  E  K  N  L  Q  A  N  K  K  R  G  E  Y  S          486
```

FIG. 4B.

```
AAGACAGATGTCCGTTGCCTGAACTAAACTATAATCATCCCTGAACTAAGAGCCTTGGAAGCATTGCTCGAAATTCT    1539
  K  T  D  V  R  L  P  E  L  N  Y  N  H  L  P  E  L  R  A  L  E  G  I  A  R  N  S       513
AGGCTCATAAGAAGGAGAACAAAATTCTTTCAGAATCTCGAATTCCTTCTCTGGCTGCCATTGACCTGCACACACCCAAC   1620
  R  L  I  R  K  E  N  K  I  L  S  E  S  R  I  P  S  L  A  A  I  D  L  H  T  P  N       540
ATTGCAGTACATCAGGTGTCAGGATCTCCCCTGTCAGAGGCCGATTCGCCTTGGATGGAGCACCAGCACTGA            1701
  I  A  V  H  Q  V  S  G  S  P  L  S  D  G  S  E  A  D  S  P  W  M  E  H  Q  H  *       566
AGATCACTTGGTGTGGTTCTCTGATCTGGATGCTGCTGTAGCTCTGAACAAAGCTGCTGATATCCTA                 1782
GGAGGAGAGATGAGCGCTTTTGAGGGTTTGCCTCTGAACTGCCTGTGTTTTCTAAGAAAGCTTTGCAGAAGAAGAACGA     1863
CAAAGACTTGGAGATGTTTCAAAAGAAGATTGAACAAGTACTACTCATCCCCACTGTTATCCCATCACCTTTCAAGTCCACTGA 1944
TGCTATTCAAGATGTATCTAGAAAGAGGGTGATGTGATTCTGTTACATGAAGTGTATTTGCTGTTAGAAAACTGTGT      2025
ATTTAAAGTTATGTAAGATTAAAGTGAGTGAGAAAGAAGAGATATTACAAAATGTCATGCATTGAACTTTGTGTTAT      2106
CTGTATAAATGTAAGCATTTATGTGGAGGCTTGATGGGGGTGTAAGAAAACTGGATCAGTGAGTAAGAGAAACTGTTT     2187
CCTTTACCCTAACTAACTCCAAAATATCTTTTAGTTTCTGATTACTGCTGAGTTGGTCAGTGTATTGTGACCTCTGTACTGGTA 2268
ATCCATGGAAAGATGAATATCTTTATTCTAATGATTTAGTGCAAGTCTGACATTGAGAGTCCTC                   2349
TAAGAACTACTATAATGCAAATCTGGCAGTGAACCTTTTATTCTAATGATTTAGTGCAAGTCTGACATTGAGAGTCCTC   2430
TGTATTTTAAGATTCTGGTGCTAAATGTTCCTGTGTGAAGAACATAATTGGCAGAAAAGTGGAGGAGGAGGGTTTGTTC   2511
TAAAAAAAAAAAGAAGTATACACAAGATAGGAGAAACGGGATGCCTGTGGATCAGGATGGACTACTTTCTC           2592
TGGGCAGTTGCTGTTGGACCAGTTCGAGGTGATGAGGAGGATGAAGGAGTGTCCTTTGGATTCCACTCTTACC         2673
CATTGATAGTTTGAGAGAGACTAGCAAAGGAGTTCCTGTTTGTCCTTAAACATTTAGGCCTTCCCAAAAGCTTTTC      2754
ACCAGAGTGAAAGTCATTTATCGCATTCCAAACATCTTTCTAATGCGAGGTCCACAAATTTTTAGTTAGGGCCG        2832
```

FIG. 4C.

```
Rabbit KKIAMRE     (SEQ ID NO: 4)    MEKYENLGLVGEGSYGMVKCRNKDSGRIVAIK
Human p56KKIAMRE   (SEQ ID NO: 10)   --------------------------------T---
Human p42KKIALRE   (SEQ ID NO: 11)   M-----KI-KI---------V-F-----R---Q---
Human cdc2         (SEQ ID NO: 12)   --D-TKIEKI---T--V-Y-G-H-TT-QV--M-
Human cdk2         (SEQ ID NO: 13)   --NFQKVEKI---T--V-Y-A---LT-EV--L-
Human ERK1         (SEQ ID NO: 14) MAAAAAQGGGGGGEPRRTEGVGPGVPGEVEMVKGQPFDVGPR-TQ-QYI--A----SSAYDHVRKTR
Murine p38         (SEQ ID NO: 15)           MSQERP..TFYRQELNKT.IWEVPER-Q--SP--S-A--S-CAAFDTKT-LR--V-
Human JNK1         (SEQ ID NO: 16)           MSRSKRDNNFYSVEIGDS.TFTVLKR-Q--KPI-S-AQ--I-CAAYDAILE-N----

Rabbit KKIAMRE       KFLESDDDKMVKKIAMREIKLLKQLRHENLVNLLEVCKKKRW......YLVFEFVDHTILDDLELFPNG..
Human p56KKIAMRE     --------------------------------------------.....-------------------..
Human p42KKIALRE     ----E--PVI----L---RM-----K-P------FRR-R-L...H---YC---V-HE-DRYQR-..
Human cdc2          -IR--EEEG-PST-I--S---E--P-I-S-QD-LMQDS-L........I---LSMDLKKY-DSI-P-QY
Human cdk2          -IR-DTETEG-PST-I---S---E-N-P-I-K--D-IHTENKL........---LHQDLKKFMDASALTG.
Human ERK1          -IS.PFEHQTYCQRTL---QI-LRF----VIGIRDIL.RASTLEAMRDV-I-QDLMETDLYKL-K....SQQ
Murine p38          -LSRPFQSIIHA-RTY---LR---HMK--VIG--D-FTPARSLEEFNDV--THLMGADLNNIVK.....CQK
Human JNK1          -LSRPFQNQTHA-R-Y--LV-M-CVK-K-IIG--N-FTPQ-SLEEFQDV-I-M--LM-ANLCQVIQ.....ME Rabbit KKIAMRE       LDDQVVQKYLFQIINGIGFCHSHNIIHRDIKPENILVSQSGVVKLCDFGFARTLAAP...GEVYTDYVATRW
Human p56KKIAMRE     --Y--------------------------------------------------------------------
Human p42KKIALRE     VPEHL-KSITW-TLQAVN---K-C---V-----ITKHS-I------L-TG-...SDY----
Human cdc2          M-SSL-KS--Y--LQ-V---RRVL--L-Q-L-IDDK-TI--A--L-AFGI--IR--HE-V-L-
Human cdk2          IPLPLI-SY--LLQ-LA---RVL--L-Q-L-INTE-AI--A--L-AFGV-..-VRT--HE-V-L-
Human ERK1          -SNDHICYF--Y--LR-LXYI--A-VL--L--S-L-INTTCDL-I----L--IADPEHDHTGFL-E-----
Murine p38          -TDDH--FLIY--LR-LKIY--AD-----L--S-LA-NEDCEL-IL---L--HTDDE......M-G------
Human JNK1          --HERMSYL-Y-MLC--KHL--AG----L--S--V-KSDCTL-IL---L---AGTSF....L--MN-P--V--Y
```

FIG. 5A.

```
Rabbit KKIAMRE       YRAPELLVGDVKYGKAVDWAIGCLVTEMLMGEPLFPGDSDIDQLYLIMRCLGNLIPRHQELFYKNPVFAGV
Human p56KKIAMRE     ----------------------------------------------------H--M-------------N-----
Human p42KKIALRE     --------------------F--------------------------------H--M---------------
Human cdc2           --S------DTQ--PP-------VFA-L-S-V--W--K--V------R-T--D------QV-ST-QY-S--
Human cdk2           --S--V-L-SAR-STP---I-S--TIFA-LATKK---H---E----FR-F-A---.TPNN-VWPEVESLQDY
Human ERK1           ----I-L-CKY-ST----I-SL--IFA--VTRRA------E-----FR-F-T--...TPDEVVWPGVTSMPDY
Murine p38           ----IMLNSKG-T-SI--I-SV--ILA--SNR-I---KHYL---NH-LGI--SPSQEDLNCIINMKA.RNY
Human JNK1           ----IMLNWMH-NQT--I-SV--IMA-L-T-RT----TDH----K--L-LV-TPGAELLKKISSESA.RNY
                     ----VIL-.MG-KEN--L-SV--IMG--VCHKI---RDY---WNKVIEQ--TPC-EFMKKL.QPT-.RTY Rabbit KKIAMRE       RLPEIK.ESEPLERRYPKL..............SEVVIDLAKKCLHVDPDKRPFCAELLHDFF.....QMDGF
Human p56KKIAMRE     -------R------------------------------I----------------------------------
Human p42KKIALRE     KI-DPE.DM-----LKF-NI........-YPALG-L-G---M--TE-LT-EQ-----PY-ENI.REIEDL
Human cdc2           KNTFP-WKPGS-ASHVKN-...........D-NGL--LS-M-IY--A--ISGKMA-N-PY-NDLDNQIKKM*
Human cdk2           KPSFP-WARQDFSKVV-P-...........D-DGRS-LSQM-HY--N--ISAKAA-A-P--QDVTKPVHL
Human ERK1           LQSLPSKTKVAWAKLF--............SDSKAL--LDRM-TFN-N--ITVE-A-A-PYLEQYYDPT-.E
Murine p38           IQSLAQMPKMNFANVFIG............ANPLAV--LE-M-VL-S---ITA-QA-A-AY-AQYHDPD-.E
Human JNK1           VENRP-YAGYSF-KLF-DVLFPADSEHNKLKASQAR--LS-M-VI-AS--ISVD-A-Q-PYINVWYDPSEAE Rabbit KKIAMRE       A...ERFSQELQMKVQKDARNISLSKKSQNRKKEKEKDDSLGEERKTLVVQDTNVDSKFKDSKVFKIKGSKI
Human p56KKIAMRE     -...:-------L-------V--------------V------A-P-I--Y-L----
Human p42KKIALRE     -...KEHDKPTRKTLR-SRKHHCFTET-KLQYLPQLTGS-IL...PA-DNKKYYC-T-KLNYRFPN-*
Human cdc2           RL*
Human cdk2           PVAE-P-TFAMELDDLPKE-LKE-IFQETA-FQPGVLEAP*
Human ERK1           FVAD.PYDQSFESRDLLIDEWK--TYDEVISFVPPPL-QEEM-S*
Murine p38           -PPPKIPDKQ-DEREHTIEEWKE-IY-EVMDLE-RT-NGVIRGQPSP-AQVQQ*
Human JNK1

Rabbit KKIAMRE       DGEKVDKGNRAAVSMTVGPSHIKAVPSTSLRDCSNVSVDHTRNPGMAIPRLTHNLSAVAPGINSGMGTIPGV
Human p56KKIAMRE     ----AE-------........-N-I-----K---------------SV---P--------S---------I.
```

FIG. 5B.

```
Rabbit KKIAMRE     QSYRVDEKTKKYCIPFVKPNKHSPSGIYNMNVTTSVSSEKNLLQANKKRGEYSKTDVRLPELNYNHLPELRA
Human p56KKIAMRE   -G------CS-------R--------I----L--................................

Rabbit KKIAMRE     LEGIARNSRLIRKENKILSESRIPSLAAIDLHTPNIAVHQVSGSPLSDGSEADSPWMEHQH*
Human p56KKIAMRE   ...................................P----D-G--L-Q-----*
```

FIG. 5C.

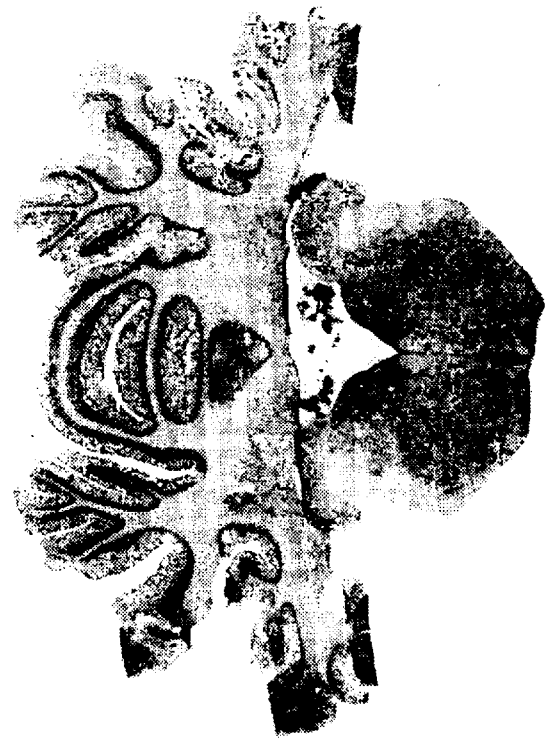
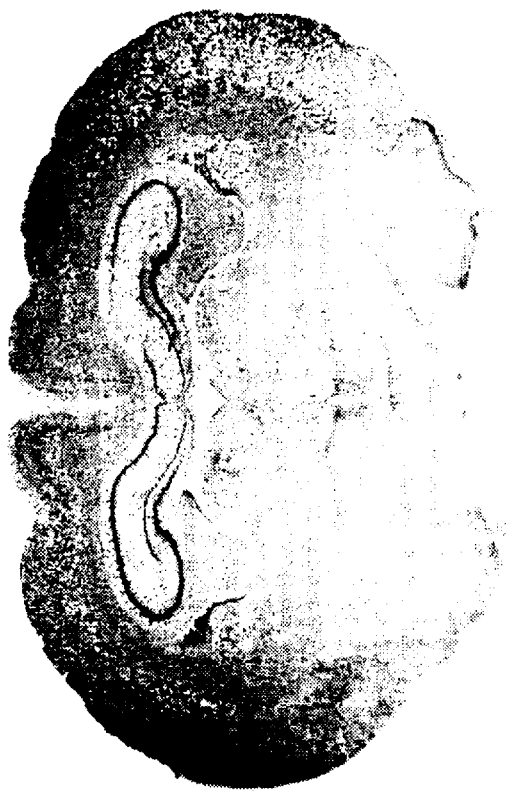
FIG. 7.

SEQ ID NO: 5

ATGGAAAAATATGAGAACCTTGGATTGGTTGGAGAAGGGAGTTATGGAATGGTGATGAAGT
GTAGGAATAAAGATAGTGGAAGAATTGTGGCCATCAAGAAGTTCCTAGAAAGTGATGATGA
CAAAATGGTTAAAAAAATTGCTATGCGAGAAATCAAGTTACTAAAGCAACTGAGGCATGAA
AATTTGGTGAATCTGTTGGAGGTGTGTAAAAAAAAAAACGATGGTACCTAGTCTTTGAAT
TTGTTGACCACACGATTCTTGATGACTTGGAACTCTTTCCAAATGGACTAGATGACCAAGT
AGTTCAAAGTATTTGTTTCAGATTATTAATGGAATTGGATTTTGTCACAGTCACAATATC
ATACATAGAGATATAAAGCCAGAGAATATATTGGTCTCCCAGTCTGGCGTTGTCAAGTTAT
GTGATTTTGGATTTGCACGGACACTGGCAGCTCCCGGAGAGGTTTACACTGATTATGTGGC
AACTCGATGGTACAGAGCTCCAGAACTACTGGTTGGTGATGTCAAGTATGGCAAAGCTGTG
GATGTGTGGGCCATTGGTTGTCTGGTAACTGAAATGCTCATGGGGGAACCCCTGTTTCCTG
GAGACTCTGATATTGATCAGCTTTATCTTATTATGAGGTGTTTAGGTAATCTAATTCCAAG
ACACCAGGAGCTTTTTTATAAAAATCCTGTGTTTGCTGGAGTAAGGTTGCCTGAAATCAAG
GAATCAGAACCTCTTGAAAGACGCTATCCCAAGCTCTCAGAAGTTGTGATAGATTTAGCAA
AGAAATGCTTACATGTTGACCCAGACAAAAGGCCCTTCTGTGCTGAGCTCCTACACCATGA
TTTCTTTCAGATGGATGGATTTGCTGAGCGGTTTTCTCAGGAACTACAGATGAAAGTACAG
AAAGATGCCAGAAATATATCTTTATCTAAAAAATCCCAGAACAGAAAGAAGGAAAAGGAAA
AGGATGATTCCTTAGGCGAAGAAAGAAAAACACTAGTGGTACAGGATACCAATGTTGACTC
CAAATTTAAGGATTCTAAAGTATTTAAAATAAAAGGATCAAAAATTGATGGAGAAAAAGTT
GACAAAGGCAATAGAGCAGCTGTCTCCATGACAGTGGGACCAAGCCACATCAAAGCAGTGC
CTTCCACAAGCCTCAGAGACTGCAGCAATGTCAGTGTGGATCACACAAGGAATCCAGGCAT
GGCCATTCCCCGCCTTACGCACAATCTTTCTGCAGTTGCTCCTGGAATTAATTCTGGAATG
GGGACTATCCCAGGAGTTCAGAGTTACAGAGTGGATGAGAAGACTAAGAAGTATTGTATTC
CATTTGTTAAGCCAAATAAACATTCTCCATCAGGCATTTATAATATGAATGTGACCACATC
AGTCTCCAGTGAAAAGAACCTCCTTCAGGCAAACAAGAAAGAGGGGAGTACTCCAAGACA
GATGTCCGTTTGCCTGAACTAAACTATAATCATCTCCCTGAACTAAGAGCCTTGGAAGGCA
TTGCTCGAAATTCTAGGCTCATAAGAAAGGAGAACAAAATTCTTTCAGAATCTCGAATTCC
TTCTCTGGCTGCCATTGACCTGCACACACCCAACATTGCAGTACATCAGGTGTCAGGATCT
CCCCTGTCAGATGGTTCAGAGGCCGATTCGCCTTGGATGGAGCACCAGCAC

*FIG. 9.*

SEQUENCE LISTING

```
<160> NUMBER OF SEQ ID NOS: 16

<210> SEQ ID NO 1
<211> LENGTH: 16
<212> TYPE: DNA
<213> ORGANISM: Artificial Sequence
<220> FEATURE:
<223> OTHER INFORMATION: Anchored primer

<400> SEQUENCE: 1
aagctttttt tttta                                                    16

<210> SEQ ID NO 2
<211> LENGTH: 13
<212> TYPE: DNA
<213> ORGANISM: Artificial Sequence
<220> FEATURE:
<223> OTHER INFORMATION: Random arbitrary primer
```

-continued

```
<400> SEQUENCE: 2
aagctttggt cag                                                        13

<210> SEQ ID NO 3
<211> LENGTH: 3080
<212> TYPE: DNA
<213> ORGANISM: Orcytolagus cuniculus
<220> FEATURE:
<221> NAME/KEY: CDS
<222> LOCATION: (249)...(1949)

<400> SEQUENCE: 3
cggccctgcg aggtgcgagc ttgggccggc gggcgaggcg gctcggcctc cctgcctgct      60
tcccccgggg gccgggactg cgtcggcggg gtctgtcgcg cggcgctggg gctgctggtg     120
tgcagggcag cgtcttctag acctgcgagc gacatgcatt tcgcctcaga tgtgttccca     180
agttgaaaac cttccatgcg agaggatttg aagaaagaga ataaaaattc tacgggcttt     240 aaattaaa atg gaa aaa tat gag aac ctt gga ttg gtt gga gaa ggg agt     290
         Met Glu Lys Tyr Glu Asn Leu Gly Leu Val Gly Glu Gly Ser
           1               5                   10 tat gga atg gtg atg aag tgt agg aat aaa gat agt gga aga att gtg     338
Tyr Gly Met Val Met Lys Cys Arg Asn Lys Asp Ser Gly Arg Ile Val
 15                  20                  25                  30 gcc atc aag aag ttc cta gaa agt gat gat gac aaa atg gtt aaa aaa     386
Ala Ile Lys Lys Phe Leu Glu Ser Asp Asp Asp Lys Met Val Lys Lys
                 35                  40                  45 att gct atg cga gaa atc aag tta cta aag caa ctg agg cat gaa aat     434
Ile Ala Met Arg Glu Ile Lys Leu Leu Lys Gln Leu Arg His Glu Asn
             50                  55                  60 ttg gtg aat ctg ttg gag gtg tgt aaa aaa aaa aaa cga tgg tac cta     482
Leu Val Asn Leu Leu Glu Val Cys Lys Lys Lys Lys Arg Trp Tyr Leu
         65                  70                  75 gtc ttt gaa ttt gtt gac cac acg att ctt gat gac ttg gaa ctc ttt     530
Val Phe Glu Phe Val Asp His Thr Ile Leu Asp Asp Leu Glu Leu Phe
     80                  85                  90 cca aat gga cta gat gac caa gta gtt caa aag tat ttg ttt cag att     578
Pro Asn Gly Leu Asp Asp Gln Val Val Gln Lys Tyr Leu Phe Gln Ile
 95                 100                 105                 110 att aat gga att gga ttt tgt cac agt cac aat atc ata cat aga gat     626
Ile Asn Gly Ile Gly Phe Cys His Ser His Asn Ile Ile His Arg Asp
                115                 120                 125 ata aag cca gag aat ata ttg gtc tcc cag tct ggc gtt gtc aag tta     674
Ile Lys Pro Glu Asn Ile Leu Val Ser Gln Ser Gly Val Val Lys Leu
            130                 135                 140 tgt gat ttt gga ttt gca cgg aca ctg gca gct ccc gga gag gtt tac     722
Cys Asp Phe Gly Phe Ala Arg Thr Leu Ala Ala Pro Gly Glu Val Tyr
        145                 150                 155 act gat tat gtg gca act cga tgg tac aga gct cca gaa cta ctg gtt     770
Thr Asp Tyr Val Ala Thr Arg Trp Tyr Arg Ala Pro Glu Leu Leu Val
    160                 165                 170 ggt gat gtc aag tat ggc aaa gct gtg gat gtg tgg gcc att ggt tgt     818
Gly Asp Val Lys Tyr Gly Lys Ala Val Asp Val Trp Ala Ile Gly Cys
175                 180                 185                 190 ctg gta act gaa atg ctc atg ggg gaa ccc ctg ttt cct gga gac tct     866
Leu Val Thr Glu Met Leu Met Gly Glu Pro Leu Phe Pro Gly Asp Ser
                195                 200                 205 gat att gat cag ctt tat ctt att atg agg tgt tta ggt aat cta att     914
Asp Ile Asp Gln Leu Tyr Leu Ile Met Arg Cys Leu Gly Asn Leu Ile
            210                 215                 220
```

-continued

| | |
|---|---|
| cca aga cac cag gag ctt ttt tat aaa aat cct gtg ttt gct gga gta<br>Pro Arg His Gln Glu Leu Phe Tyr Lys Asn Pro Val Phe Ala Gly Val<br>225 230 235 | 962 |
| agg ttg cct gaa atc aag gaa tca gaa cct ctt gaa aga cgc tat ccc<br>Arg Leu Pro Glu Ile Lys Glu Ser Glu Pro Leu Glu Arg Arg Tyr Pro<br>240 245 250 | 1010 |
| aag ctc tca gaa gtt gtg ata gat tta gca aag aaa tgc tta cat gtt<br>Lys Leu Ser Glu Val Val Ile Asp Leu Ala Lys Lys Cys Leu His Val<br>255 260 265 270 | 1058 |
| gac cca gac aaa agg ccc ttc tgt gct gag ctc cta cac cat gat ttc<br>Asp Pro Asp Lys Arg Pro Phe Cys Ala Glu Leu Leu His His Asp Phe<br>275 280 285 | 1106 |
| ttt cag atg gat gga ttt gct gag cgg ttt tct cag gaa cta cag atg<br>Phe Gln Met Asp Gly Phe Ala Glu Arg Phe Ser Gln Glu Leu Gln Met<br>290 295 300 | 1154 |
| aaa gta cag aaa gat gcc aga aat ata tct tta tct aaa aaa tcc cag<br>Lys Val Gln Lys Asp Ala Arg Asn Ile Ser Leu Ser Lys Lys Ser Gln<br>305 310 315 | 1202 |
| aac aga aag aag gaa aag gaa aag gat gat tcc tta ggc gaa gaa aga<br>Asn Arg Lys Lys Glu Lys Glu Lys Asp Asp Ser Leu Gly Glu Glu Arg<br>320 325 330 | 1250 |
| aaa aca cta gtg gta cag gat acc aat gtt gac tcc aaa ttt aag gat<br>Lys Thr Leu Val Val Gln Asp Thr Asn Val Asp Ser Lys Phe Lys Asp<br>335 340 345 350 | 1298 |
| tct aaa gta ttt aaa ata aaa gga tca aaa att gat gga gaa aaa gtt<br>Ser Lys Val Phe Lys Ile Lys Gly Ser Lys Ile Asp Gly Glu Lys Val<br>355 360 365 | 1346 |
| gac aaa ggc aat aga gca gct gtc tcc atg aca gtg gga cca agc cac<br>Asp Lys Gly Asn Arg Ala Ala Val Ser Met Thr Val Gly Pro Ser His<br>370 375 380 | 1394 |
| atc aaa gca gtg cct tcc aca agc ctc aga gac tgc agc aat gtc agt<br>Ile Lys Ala Val Pro Ser Thr Ser Leu Arg Asp Cys Ser Asn Val Ser<br>385 390 395 | 1442 |
| gtg gat cac aca agg aat cca ggc atg gcc att ccc cgc ctt acg cac<br>Val Asp His Thr Arg Asn Pro Gly Met Ala Ile Pro Arg Leu Thr His<br>400 405 410 | 1490 |
| aat ctt tct gca gtt gct cct gga att aat tct gga atg ggg act atc<br>Asn Leu Ser Ala Val Ala Pro Gly Ile Asn Ser Gly Met Gly Thr Ile<br>415 420 425 430 | 1538 |
| cca gga gtt cag agt tac aga gtg gat gag aag act aag aag tat tgt<br>Pro Gly Val Gln Ser Tyr Arg Val Asp Glu Lys Thr Lys Lys Tyr Cys<br>435 440 445 | 1586 |
| att cca ttt gtt aag cca aat aaa cat tct cca tca ggc att tat aat<br>Ile Pro Phe Val Lys Pro Asn Lys His Ser Pro Ser Gly Ile Tyr Asn<br>450 455 460 | 1634 |
| atg aat gtg acc aca tca gtc tcc agt gaa aag aac ctc ctt cag gca<br>Met Asn Val Thr Thr Ser Val Ser Ser Glu Lys Asn Leu Leu Gln Ala<br>465 470 475 | 1682 |
| aac aag aaa aga ggg gag tac tcc aag aca gat gtc cgt ttg cct gaa<br>Asn Lys Lys Arg Gly Glu Tyr Ser Lys Thr Asp Val Arg Leu Pro Glu<br>480 485 490 | 1730 |
| cta aac tat aat cat ctc cct gaa cta aga gcc ttg gaa ggc att gct<br>Leu Asn Tyr Asn His Leu Pro Glu Leu Arg Ala Leu Glu Gly Ile Ala<br>495 500 505 510 | 1778 |
| cga aat tct agg ctc ata aga aag gag aac aaa att ctt tca gaa tct<br>Arg Asn Ser Arg Leu Ile Arg Lys Glu Asn Lys Ile Leu Ser Glu Ser<br>515 520 525 | 1826 |
| cga att cct tct ctg gct gcc att gac ctg cac aca ccc aac att gca<br>Arg Ile Pro Ser Leu Ala Ala Ile Asp Leu His Thr Pro Asn Ile Ala<br>530 535 540 | 1874 |

-continued

```
gta cat cag gtg tca gga tct ccc ctg tca gat ggt tca gag gcc gat     1922
Val His Gln Val Ser Gly Ser Pro Leu Ser Asp Gly Ser Glu Ala Asp
        545                 550                 555 tcg cct tgg atg gag cac cag cac tga agatcacttg gtggttctga           1969
Ser Pro Trp Met Glu His Gln His
    560                 565 tctggatgct gctgtagctc ttgggatggc accctctccc aacaaagctg ctgatatcct   2029
aggaggagag atgagcgctt tgagggtttt gcctctgaac tgcctgtgtt ttctaagaaa   2089
ggctttgcag aagaaggaac gacaaagact tggagatgtt tcaaaagaag attgaacaag   2149
tactcatccc cactgttatc ccatcacctt tcaagtccac tgatgctatt tcaagatgta   2209
tctagaaaga ggggtgatgt gattcttgtt acatgaatgt gtatttgctg ttagaaaact   2269
gtgtatttaa agttatgtaa gattaaaagt gagtgagaaa agaagagaga tattacaaaa   2329
tgtcatgcat tgaactttgt gttatctgta taaatgtaag catttatgtg ggagtgggct   2389
tgatgggggg tggtaagaaa actgggatca gtaagagaaa ctgtttcctt taccctaact   2449
taactccaaa aatatacttc aaaaaatctc acttattttt aggcagaaag agatgtaggt   2509
aactgccatc catggaaaga tgaatatctt ttagtttctg tgattactgc tgatgtttgg   2569
tcagtgtatt gtgacctctg tactggtata agaactacta taatgcaaat ctggcagtga   2629
aaccttttat ttctaatgat ttagtgcaag tctgacattg agagtcctct gtattttaag   2689
attctggtgc taaatgttcc tgtgtggaag aacataattg gcagaaaagt ggaggaggag   2749
gggtttgttc taaaaaaaaa aaagaagtat acacacaaga taggagatgg gaaacgggat   2809
ggcctgtgga tcaggatgga ctactttct ctgggcagtt gctgttggac cagttcgagg   2869
tgatgagaga ggataggatg gaagggagtg tcctttggat tccactctta cccattgata   2929
gtttgagaga gactagcaaa ggagttcctg tccgtttgtt ccttaaacat ttaggccttc   2989
ccaaaagctt ttcaccagag tgaaaagtca tttatctgca ttccaaacat ctttctaat   3049
gcgagggtcc acaaattttt agttagggcc g                                  3080
```

<210> SEQ ID NO 4
<211> LENGTH: 566
<212> TYPE: PRT
<213> ORGANISM: Orcytolagus cuniculus

<400> SEQUENCE: 4

```
Met Glu Lys Tyr Glu Asn Leu Gly Leu Val Gly Glu Gly Ser Tyr Gly
  1               5                  10                  15

Met Val Met Lys Cys Arg Asn Lys Asp Ser Gly Arg Ile Val Ala Ile
             20                  25                  30

Lys Lys Phe Leu Glu Ser Asp Asp Asp Lys Met Val Lys Lys Ile Ala
         35                  40                  45

Met Arg Glu Ile Lys Leu Leu Lys Gln Leu Arg His Glu Asn Leu Val
     50                  55                  60

Asn Leu Leu Glu Val Cys Lys Lys Lys Arg Trp Tyr Leu Val Phe
 65                  70                  75                  80

Glu Phe Val Asp His Thr Ile Leu Asp Asp Leu Glu Leu Phe Pro Asn
                 85                  90                  95

Gly Leu Asp Asp Gln Val Val Gln Lys Tyr Leu Phe Gln Ile Ile Asn
            100                 105                 110

Gly Ile Gly Phe Cys His Ser His Asn Ile Ile His Arg Asp Ile Lys
        115                 120                 125
```

-continued

```
Pro Glu Asn Ile Leu Val Ser Gln Ser Gly Val Val Lys Leu Cys Asp
130                 135                 140

Phe Gly Phe Ala Arg Thr Leu Ala Ala Pro Gly Glu Val Tyr Thr Asp
145                 150                 155                 160

Tyr Val Ala Thr Arg Trp Tyr Arg Ala Pro Glu Leu Leu Val Gly Asp
                165                 170                 175

Val Lys Tyr Gly Lys Ala Val Asp Val Trp Ala Ile Gly Cys Leu Val
                180                 185                 190

Thr Glu Met Leu Met Gly Glu Pro Leu Phe Pro Gly Asp Ser Asp Ile
                195                 200                 205

Asp Gln Leu Tyr Leu Ile Met Arg Cys Leu Gly Asn Leu Ile Pro Arg
210                 215                 220

His Gln Glu Leu Phe Tyr Lys Asn Pro Val Phe Ala Gly Val Arg Leu
225                 230                 235                 240

Pro Glu Ile Lys Glu Ser Glu Pro Leu Glu Arg Arg Tyr Pro Lys Leu
                245                 250                 255

Ser Glu Val Val Ile Asp Leu Ala Lys Lys Cys Leu His Val Asp Pro
                260                 265                 270

Asp Lys Arg Pro Phe Cys Ala Glu Leu Leu His His Asp Phe Phe Gln
        275                 280                 285

Met Asp Gly Phe Ala Glu Arg Phe Ser Gln Glu Leu Gln Met Lys Val
290                 295                 300

Gln Lys Asp Ala Arg Asn Ile Ser Leu Ser Lys Lys Ser Gln Asn Arg
305                 310                 315                 320

Lys Lys Glu Lys Glu Lys Asp Asp Ser Leu Gly Glu Glu Arg Lys Thr
                325                 330                 335

Leu Val Val Gln Asp Thr Asn Val Asp Ser Lys Phe Lys Asp Ser Lys
                340                 345                 350

Val Phe Lys Ile Lys Gly Ser Lys Ile Asp Gly Glu Lys Val Asp Lys
                355                 360                 365

Gly Asn Arg Ala Ala Val Ser Met Thr Val Gly Pro Ser His Ile Lys
370                 375                 380

Ala Val Pro Ser Thr Ser Leu Arg Asp Cys Ser Asn Val Ser Val Asp
385                 390                 395                 400

His Thr Arg Asn Pro Gly Met Ala Ile Pro Arg Leu Thr His Asn Leu
                405                 410                 415

Ser Ala Val Ala Pro Gly Ile Asn Ser Gly Met Gly Thr Ile Pro Gly
                420                 425                 430

Val Gln Ser Tyr Arg Val Asp Glu Lys Thr Lys Tyr Cys Ile Pro
                435                 440                 445

Phe Val Lys Pro Asn Lys His Ser Pro Ser Gly Ile Tyr Asn Met Asn
450                 455                 460

Val Thr Thr Ser Val Ser Ser Glu Lys Asn Leu Leu Gln Ala Asn Lys
465                 470                 475                 480

Lys Arg Gly Glu Tyr Ser Lys Thr Asp Val Arg Leu Pro Glu Leu Asn
                485                 490                 495

Tyr Asn His Leu Pro Glu Leu Arg Ala Leu Glu Gly Ile Ala Arg Asn
                500                 505                 510

Ser Arg Leu Ile Arg Lys Glu Asn Lys Ile Leu Ser Glu Ser Arg Ile
                515                 520                 525

Pro Ser Leu Ala Ala Ile Asp Leu His Thr Pro Asn Ile Ala Val His
530                 535                 540
```

```
Gln Val Ser Gly Ser Pro Leu Ser Asp Gly Ser Glu Ala Asp Ser Pro
545                 550                 555                 560

Trp Met Glu His Gln His
            565
```

<210> SEQ ID NO 5
<211> LENGTH: 1701
<212> TYPE: DNA
<213> ORGANISM: Orcytolagus cuniculus

<400> SEQUENCE: 5

```
atggaaaaat atgagaacct tggattggtt ggagaaggga gttatggaat ggtgatgaag      60
tgtaggaata agatagtgg aagaattgtg gccatcaaga agttcctaga aagtgatgat     120
gacaaaatgg ttaaaaaaat tgctatgcga gaaatcaagt tactaaagca actgaggcat     180
gaaaatttgg tgaatctgtt ggaggtgtgt aaaaaaaaaa aacgatggta cctagtcttt     240
gaatttgttg accacacgat tcttgatgac ttggaactct ttccaaatgg actagatgac     300
caagtagttc aaaagtattt gtttcagatt attaatggaa ttggattttg tcacagtcac     360
aatatcatac atagagatat aaagccagag aatatattgg tctcccagtc tggcgttgtc     420
aagttatgtg attttggatt tgcacggaca ctggcagctc ccggagaggt ttacactgat     480
tatgtggcaa ctcgatggta cagagctcca gaactactgg ttggtgatgt caagtatggc     540
aaagctgtgg atgtgtgggc cattggttgt ctggtaactg aaatgctcat ggggaaccc     600
ctgtttcctg gagactctga tattgatcag ctttatctta ttatgaggtg tttaggtaat     660
ctaattccaa gacaccagga gctttttat aaaaatcctg tgtttgctgg agtaaggttg     720
cctgaaatca ggaatcaga acctcttgaa agacgctatc ccaagctctc agaagttgtg     780
atagatttag caagaaatg cttacatgtt gacccagaca aaggcccctt ctgtgctgag     840
ctcctacacc atgatttctt tcagatggat ggatttgctg agcggttttc tcaggaacta     900
cagatgaaag tacagaaaga tgccagaaat atatctttat ctaaaaaatc ccagaacaga     960
aagaaggaaa aggaaaagga tgattcctta ggcgaagaaa gaaaaacact agtggtacag    1020
gataccaatg ttgactccaa atttaaggat tctaaagtat ttaaaataaa aggatcaaaa    1080
attgatggag aaaaagttga caaaggcaat agagcagctg tctccatgac agtgggacca    1140
agccacatca aagcagtgcc ttccacaagc ctcagagact gcagcaatgt cagtgtggat    1200
cacacaagga atccaggcat ggccattccc cgccttacgc acaatctttc tgcagttgct    1260
cctggaatta attctggaat ggggactatc ccaggagttc agagttacag agtggatgag    1320
aagactaaga agtattgtat tccatttgtt aagccaaata acattctcc atcaggcatt    1380
tataatatga atgtgaccac atcagtctcc agtgaaaaga acctccttca ggcaaacaag    1440
aaaagagggg agtactccaa gacagatgtc cgtttgcctg aactaaacta taatcatctc    1500
cctgaactaa gagccttgga aggcattgct cgaaattcta ggctcataag aaaggagaac    1560
aaaattcttt cagaatctcg aattccttct ctggctgcca ttgacctgca cacacccaac    1620
attgcagtac atcaggtgtc aggatctccc ctgtcagatg gttcagaggc cgattcgcct    1680
tggatggagc accagcactg a                                              1701
```

<210> SEQ ID NO 6
<211> LENGTH: 20
<212> TYPE: DNA
<213> ORGANISM: Artificial Sequence
<220> FEATURE:
<223> OTHER INFORMATION: PCR primer

```
<400> SEQUENCE: 6
ttgcagaaga aggaacgaca                                              20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
tgtcgttcct tcttctgcaa                                              20

<210> SEQ ID NO 8
<211> LENGTH: 20
<212> TYPE: DNA
<213> ORGANISM: Artificial Sequence
<220> FEATURE:
<223> OTHER INFORMATION: Sense primer

<400> SEQUENCE: 8
aaggccaaga ccctggagat                                              20

<210> SEQ ID NO 9
<211> LENGTH: 20
<212> TYPE: DNA
<213> ORGANISM: Artificial Sequence
<220> FEATURE:
<223> OTHER INFORMATION: Antisense primer

<400> SEQUENCE: 9
tcaatctttc ttcttggttg                                              20

<210> SEQ ID NO 10
<211> LENGTH: 493
<212> TYPE: PRT
<213> ORGANISM: Homo sapiens

<400> SEQUENCE: 10
```

Met Glu Lys Tyr Glu Asn Leu Gly Leu Val Gly Glu Gly Ser Tyr Gly
 1               5                  10                  15

Met Val Met Lys Cys Arg Asn Lys Asp Thr Gly Arg Ile Val Ala Ile
            20                  25                  30

Lys Lys Phe Leu Glu Ser Asp Asp Asp Lys Met Val Lys Lys Ile Ala
        35                  40                  45

Met Arg Glu Ile Lys Leu Leu Lys Gln Leu Arg His Glu Asn Leu Val
    50                  55                  60

Asn Leu Leu Glu Val Cys Lys Lys Lys Arg Trp Tyr Leu Val Phe
65                  70                  75                  80

Glu Phe Val Asp His Thr Ile Leu Asp Asp Leu Glu Leu Phe Pro Asn
                85                  90                  95

Gly Leu Asp Tyr Gln Val Val Gln Lys Tyr Leu Phe Gln Ile Ile Asn
            100                 105                 110

Gly Ile Gly Phe Cys His Ser His Asn Ile Ile His Arg Asp Ile Lys
        115                 120                 125

Pro Glu Asn Ile Leu Val Ser Gln Ser Gly Val Lys Leu Cys Asp
    130                 135                 140

Phe Gly Phe Ala Arg Thr Leu Ala Ala Pro Gly Glu Val Tyr Thr Asp
145                 150                 155                 160

```
Tyr Val Ala Thr Arg Trp Tyr Arg Ala Pro Glu Leu Leu Val Gly Asp
                165                 170                 175

Val Lys Tyr Gly Lys Ala Val Asp Val Trp Ala Ile Gly Cys Leu Val
            180                 185                 190

Thr Glu Met Phe Met Gly Glu Pro Leu Phe Pro Gly Asp Ser Asp Ile
        195                 200                 205

Asp Gln Leu Tyr His Ile Met Met Cys Leu Gly Asn Leu Ile Pro Arg
    210                 215                 220

His Gln Glu Leu Phe Asn Lys Asn Pro Val Phe Ala Gly Val Arg Leu
225                 230                 235                 240

Pro Glu Ile Lys Glu Arg Glu Pro Leu Glu Arg Arg Tyr Pro Lys Leu
                245                 250                 255

Ser Glu Val Val Ile Asp Leu Ala Lys Lys Cys Leu His Ile Asp Pro
            260                 265                 270

Asp Lys Arg Pro Phe Cys Ala Glu Leu Leu His His Asp Phe Phe Gln
        275                 280                 285

Met Asp Gly Phe Ala Glu Arg Phe Ser Gln Glu Leu Gln Leu Lys Val
    290                 295                 300

Gln Lys Asp Ala Arg Asn Val Ser Leu Ser Lys Ser Gln Asn Arg
305                 310                 315                 320

Lys Lys Glu Lys Glu Lys Asp Asp Ser Leu Val Glu Glu Arg Lys Thr
                325                 330                 335

Leu Val Val Gln Asp Thr Asn Ala Asp Pro Lys Ile Lys Asp Tyr Lys
            340                 345                 350

Leu Phe Lys Ile Lys Gly Ser Lys Ile Asp Gly Glu Lys Ala Glu Lys
        355                 360                 365

Gly Asn Arg Ala Ser Asn Ala Ser Cys Leu His Asp Ser Arg Thr Ser
    370                 375                 380

His Asn Lys Ile Val Pro Ser Thr Ser Leu Lys Asp Cys Ser Asn Val
385                 390                 395                 400

Ser Val Asp His Thr Arg Asn Pro Ser Val Ala Ile Pro Pro Leu Thr
                405                 410                 415

His Asn Leu Ser Ala Val Ala Pro Ser Ile Asn Ser Gly Met Gly Thr
            420                 425                 430

Glu Thr Ile Pro Ile Gln Gly Tyr Arg Val Asp Glu Lys Thr Lys Lys
        435                 440                 445

Cys Ser Ile Pro Phe Val Lys Pro Asn Arg His Ser Pro Ser Gly Ile
    450                 455                 460

Tyr Asn Ile Asn Val Thr Thr Leu Val Ser Gly Pro Pro Leu Ser Asp
465                 470                 475                 480

Asp Ser Gly Ala Asp Leu Pro Gln Met Glu His Gln His
                485                 490

<210> SEQ ID NO 11
<211> LENGTH: 358
<212> TYPE: PRT
<213> ORGANISM: Homo sapiens

<400> SEQUENCE: 11

Met Met Glu Lys Tyr Glu Lys Ile Gly Lys Ile Gly Glu Gly Ser Tyr
1               5                   10                  15

Gly Val Val Phe Lys Cys Arg Asn Arg Asp Thr Gly Gln Ile Val Ala
            20                  25                  30

Ile Lys Lys Phe Leu Glu Ser Glu Asp Asp Pro Val Ile Lys Lys Ile
        35                  40                  45
```

```
Ala Leu Arg Glu Ile Arg Met Leu Lys Gln Leu Lys His Pro Asn Leu
 50                  55                  60

Val Asn Leu Leu Glu Val Phe Arg Arg Lys Arg Arg Leu His Leu Val
 65                  70                  75                  80

Phe Glu Tyr Cys Asp His Thr Val Leu His Glu Leu Asp Arg Tyr Gln
                 85                  90                  95

Arg Gly Val Pro Glu His Leu Val Lys Ser Ile Thr Trp Gln Thr Leu
                100                 105                 110

Gln Ala Val Asn Phe Cys His Lys His Asn Cys Ile His Arg Asp Val
                115                 120                 125

Lys Pro Glu Asn Ile Leu Ile Thr Lys His Ser Val Ile Lys Leu Cys
130                 135                 140

Asp Phe Gly Phe Ala Arg Leu Leu Thr Gly Pro Ser Asp Tyr Tyr Thr
145                 150                 155                 160

Asp Tyr Val Ala Thr Arg Trp Tyr Arg Ser Pro Glu Leu Leu Val Gly
                165                 170                 175

Asp Thr Gln Tyr Gly Pro Pro Val Asp Val Trp Ala Ile Gly Cys Val
                180                 185                 190

Phe Ala Glu Leu Leu Ser Gly Val Pro Leu Trp Pro Gly Lys Ser Asp
                195                 200                 205

Val Asp Gln Leu Tyr Leu Ile Arg Lys Thr Leu Gly Asp Leu Ile Pro
210                 215                 220

Arg His Gln Gln Val Phe Ser Thr Asn Gln Tyr Phe Ser Gly Val Lys
225                 230                 235                 240

Ile Pro Asp Pro Glu Asp Met Glu Pro Leu Glu Leu Lys Phe Pro Asn
                245                 250                 255

Ile Ser Tyr Pro Ala Leu Gly Leu Leu Lys Gly Cys Leu His Met Asp
                260                 265                 270

Pro Thr Glu Arg Leu Thr Cys Glu Gln Leu Leu His His Pro Tyr Phe
                275                 280                 285

Glu Asn Ile Arg Glu Ile Glu Asp Leu Ala Lys Glu His Asp Lys Pro
290                 295                 300

Thr Arg Lys Thr Leu Arg Lys Ser Arg Lys His His Cys Phe Thr Glu
305                 310                 315                 320

Thr Ser Lys Leu Gln Tyr Leu Pro Gln Leu Thr Gly Ser Ser Ile Leu
                325                 330                 335

Pro Ala Leu Asp Asn Lys Lys Tyr Tyr Cys Asp Thr Lys Lys Leu Asn
                340                 345                 350

Tyr Arg Phe Pro Asn Ile
                355
```

<210> SEQ ID NO 12
<211> LENGTH: 297
<212> TYPE: PRT
<213> ORGANISM: Homo sapiens

<400> SEQUENCE: 12

```
Met Glu Asp Tyr Thr Lys Ile Glu Lys Ile Gly Glu Gly Thr Tyr Gly
  1               5                  10                  15

Val Val Tyr Lys Gly Arg His Lys Thr Thr Gly Gln Val Val Ala Met
                 20                  25                  30

Lys Lys Ile Arg Leu Glu Ser Glu Glu Glu Gly Val Pro Ser Thr Ala
                 35                  40                  45

Ile Arg Glu Ile Ser Leu Leu Lys Glu Leu Arg His Pro Asn Ile Val
 50                  55                  60
```

```
Ser Leu Gln Asp Val Leu Met Gln Asp Ser Arg Leu Tyr Leu Ile Phe
 65                  70                  75                  80

Glu Phe Leu Ser Met Asp Leu Lys Lys Tyr Leu Asp Ser Ile Pro Pro
                 85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
    290                 295

<210> SEQ ID NO 13
<211> LENGTH: 298
<212> TYPE: PRT
<213> ORGANISM: Homo sapiens
<220> FEATURE:
<221> NAME/KEY: VARIANT
<222> LOCATION: (1)...(298)
<223> OTHER INFORMATION: Xaa = Any Amino Acid

<400> SEQUENCE: 13

Met Glu Asn Phe Gln Lys Val Glu Lys Ile Gly Glu Gly Thr Tyr Gly
  1               5                  10                  15

Val Val Tyr Lys Ala Arg Asn Lys Leu Thr Gly Glu Val Val Ala Leu
                 20                  25                  30

Lys Lys Ile Arg Xaa Asp Thr Glu Thr Glu Gly Val Pro Ser Thr Ala
             35                  40                  45

Ile Arg Glu Ile Ser Leu Leu Lys Glu Leu Asn His Pro Asn Ile Val
 50                  55                  60

Lys Leu Leu Asp Val Ile His Thr Glu Asn Lys Leu Tyr Leu Val Phe
 65                  70                  75                  80

Glu Phe Leu His Gln Asp Leu Lys Lys Phe Met Asp Ala Ser Ala Leu
                 85                  90                  95

Thr Gly Ile Pro Leu Pro Leu Ile Lys Ser Tyr Leu Phe Gln Leu Leu
            100                 105                 110
```

```
Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
                180                 185                 190

Phe Ala Glu Met Val Thr Arg Arg Ala Leu Phe Pro Gly Asp Ser Glu
                195                 200                 205

Ile Asp Gln Leu Phe Arg Ile Phe Arg Thr Leu Gly Thr Pro Asp Glu
        210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
                260                 265                 270

Lys Arg Ile Ser Ala Lys Ala Ala Leu Ala His Pro Phe Phe Gln Asp
        275                 280                 285

Val Thr Lys Pro Val Pro His Leu Arg Leu
        290                 295
```

<210> SEQ ID NO 14
<211> LENGTH: 379
<212> TYPE: PRT
<213> ORGANISM: Rattus norvegicus

<400> SEQUENCE: 14

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
                35                  40                  45

Gly Glu Gly Ala Tyr Gly Met Val Ser Ser Ala Tyr Asp His Val Arg
        50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
        130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190
```

```
Pro Glu His Asp His Thr Gly Phe Leu Thr Glu Tyr Val Ala Thr Arg
            195                 200                 205
Trp Tyr Arg Ala Pro Glu Ile Met Leu Asn Ser Lys Gly Tyr Thr Lys
    210                 215                 220
Ser Ile Asp Ile Trp Ser Val Gly Cys Ile Leu Ala Glu Met Leu Ser
225                 230                 235                 240
Asn Arg Pro Ile Phe Pro Gly Lys His Tyr Leu Asp Gln Leu Asn His
            245                 250                 255
Ile Leu Gly Ile Leu Gly Ser Pro Ser Gln Glu Asp Leu Asn Cys Ile
            260                 265                 270
Ile Asn Met Lys Ala Arg Asn Tyr Leu Gln Ser Leu Pro Ser Lys Thr
        275                 280                 285
Lys Val Ala Trp Ala Lys Leu Phe Pro Lys Ser Asp Ser Lys Ala Leu
    290                 295                 300
Asp Leu Leu Asp Arg Met Leu Thr Phe Asn Pro Asn Lys Arg Ile Thr
305                 310                 315                 320
Val Glu Glu Ala Leu Ala His Pro Tyr Leu Glu Gln Tyr Tyr Asp Pro
                325                 330                 335
Thr Asp Glu Pro Val Ala Glu Pro Phe Thr Phe Ala Met Glu Leu
            340                 345                 350
Asp Asp Leu Pro Lys Glu Arg Leu Lys Glu Leu Ile Phe Gln Glu Thr
            355                 360                 365
Ala Arg Phe Gln Pro Gly Val Leu Glu Ala Pro
        370                 375

<210> SEQ ID NO 15
<211> LENGTH: 360
<212> TYPE: PRT
<213> ORGANISM: Mus musculus

<400> SEQUENCE: 15

Met Ser Gln Glu Arg Pro Thr Phe Tyr Arg Gln Glu Leu Asn Lys Thr
1               5                   10                  15
Ile Trp Glu Val Pro Glu Arg Tyr Gln Asn Leu Ser Pro Val Gly Ser
            20                  25                  30
Gly Ala Tyr Gly Ser Val Cys Ala Ala Phe Asp Thr Lys Thr Gly His
        35                  40                  45
Arg Val Ala Val Lys Lys Leu Ser Arg Pro Phe Gln Ser Ile Ile His
    50                  55                  60
Ala Lys Arg Thr Tyr Arg Glu Leu Arg Leu Leu Lys His Met Lys His
65                  70                  75                  80
Glu Asn Val Ile Gly Leu Leu Asp Val Phe Thr Pro Ala Arg Ser Leu
                85                  90                  95
Glu Glu Phe Asn Asp Val Tyr Leu Val Thr His Leu Met Gly Ala Asp
            100                 105                 110
Leu Asn Asn Ile Val Lys Cys Gln Lys Leu Thr Asp Asp His Val Gln
        115                 120                 125
Phe Leu Ile Tyr Gln Ile Leu Arg Gly Leu Lys Tyr Ile His Ser Ala
    130                 135                 140
Asp Ile Ile His Arg Asp Leu Lys Pro Ser Asn Leu Ala Val Asn Glu
145                 150                 155                 160
Asp Cys Glu Leu Lys Ile Leu Asp Phe Gly Leu Ala Arg His Thr Asp
                165                 170                 175
Asp Glu Met Thr Gly Tyr Val Ala Thr Arg Trp Tyr Arg Ala Pro Glu
            180                 185                 190
```

```
Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Ala Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
            355                 360

<210> SEQ ID NO 16
<211> LENGTH: 384
<212> TYPE: PRT
<213> ORGANISM: Homo sapiens

<400> SEQUENCE: 16

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205
```

-continued

```
Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
            245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Ala Gln Val Gln Gln
370                 375                 380
```

CDNA, GENOMIC, AND PREDICTED PROTEIN SEQUENCES OF LEARNING-INDUCED KINASES

RELATED APPLICATION DATA

This application is a divisional of Ser. No. 09/411,628, filed Oct. 1, 1999, now U.S. Pat. No. 6,428,994, and claims the benefit of U.S. Provisional Patent Application Ser. No. 60/102,906, filed Oct. 2, 1998, abandoned, the entire disclosures of which are hereby incorporated by reference in their entirety for all purposes.

GOVERNMENT SUPPORT

The U.S. Government has certain rights in this invention pursuant to NSF grant number IBN 9215069, and NIA grant number AF 05142.

FIELD OF THE INVENTION

The present invention provides novel polynucleotides and polypeptides encoded by such polynucleotides. This invention relates generally to the field of learning-induced protein kinases.

BACKGROUND

Classical conditioning of the eyeblink/nictitating membrane (NM) response is a useful behavioral model for investigating the neural substrates underlying basic associative learning and memory (Thompson and Krupa, 1994). Several lines of evidence have pointed to the cerebellum as a critical structure in the formation and storage of the memory trace in eyeblink conditioning. The neural output from the cerebellar (interpositus) deep nuclei to target structures forms the essential efferent pathway in this type of learning (Thompson, 1986; Krupa et al., 1993; Kim et al., 1997). The cerebellum receives projections from mossy fibers and climbing fibers, which are thought to convey information about the conditioned stimulus (CS) and unconditioned stimulus (US), respectively. The CS and US signals converge in the cerebellar cortex and deep nuclei (Ito, 1984; Thompson, 1986). The convergence of these two inputs also fulfills the condition required for the induction of cerebellar long-term depression (LTD) (Ito, 1989; Linden and Conner, 1995).

Recent studies of eyeblink conditioning in various gene knockout mice have shown that deficits in cerebellar LTD correlated with impairment in eyeblink conditioning (Aiba et al., 1994; Shibuki et al., 1996). Purkinje cell degeneration (pcd) mutant mice, which lack cortical efferents to the deep nuclei, exhibited a marked impairment in eyeblink conditioning (Chen et al., 1996), but significant learning did occur. Substantial impairment in eyeblink conditioning has also been reported in rabbits with lesions limited to cerebellar cortex (Lavond et al., 1987; Lavond and Steinmetz, 1989a; Yeo et al., 1985b). In contrast, lesions of the cerebellar deep nuclei, in particular the dorsal anterior interpositus nucleus (IN), completely prevented learning in naive animals and permanently abolished conditioned responses (CRs) in well-trained animals (Krupa, 1993; McCormick et al., 1982; Lincoln et al., 1982; Yeo et al., 1985a; Clark et al., 1992; Steinmetz et al., 1992). Such effective lesions had no persisting effects on any aspect of the reflex unconditioned response (UR) (Steinmetz et al., 1992; Ivkovich et al., 1993). Finally, reversible inactivation of the IN during training completely prevented learning but reversible inactivation of the immediate output from the IN, the superior cerebellar peduncle, and its target, the red nucleus, did not prevent learning at all (Clark and Lavond, 1996; Clark et al., 1992; Krupa et al., 1993; Krupa and Thompson, 1995; 1997; Nordholm et al., 1993); Thus, within the neural circuitry involved in eyeblink conditioning, the IN represents a critical locus for the acquisition and expression of the CR.

Much experimental evidence also supports the idea that the synthesis of new RNAs or proteins are necessary for long-term changes in synaptic efficacy associated with long-term memory formation (Agranoff, 1967; Barondes and Cohen, 1966; Davis and Squire, 1984). For example, transcription and translation inhibitors blocked long term facilitation of the gill-withdrawal reflex in Aplysia (Montarolo et al., 1986). Long term memory was further shown to require the activation of the transcription factor CREB in some animal models (Kaang et al., 1993; Bourtchuladze et al., 1994; Yin et al., 1994). As for eyeblink conditioning, infusioh of the protein synthesis inhibitor anisomycin into the IN interfered with conditioning in the rabbit (Bracha and Bloedel, 1996). In this patent, we report our studies to further unravel the molecular pathways underlying eyeblink conditioning. We first demonstrated that inhibition of RNA synthesis in the interpositus nuclear cells interfered with the acquisition of CRs. Next, we applied the method of differential display PCR (DD-PCR) (Liang and Pardee, 1992) to examine changes in gene expression that accompanied eyeblink conditioning. We identified RNA molecules that were induced with conditioning. The cDNA cloning and sequence analyses showed that the expressed gene was the KKI-AMRE kinase, a member of the cdc2-related and MAP kinase family.

SUMMARY OF THE INVENTION

The invention describes the cDNA sequence, the deduced amino acid sequence, and the genomic sequence of a learning-induced kinase, KKIAMRE kinase, expressed in rabbit brain during classical conditioning.

Polynucleotides include those with sequences substantially equivalent to including fragments thereof. Polynucleotides of the present invention also include, but are not limited to, polynucleotides complementary to the aforementioned cDNA and genomic DNA polynucleotide sequences.

Polynucleotides according to the invention have numerous applications in a variety of techniques known to those skilled in the art of molecular biology. These techniques include use as hybridization probes, use as oligomers for PCR, use as reagents to identify homologous genomic sequences, mRNA sequences, or cDNA sequences in the same or different species, use for chromosome and gene mapping, use in the recombinant production of protein, and use in generation of antisense DNA or RNA, their chemical analogs and the like. For example, when the expression of an mRNA is largely restricted to a particular cell or tissue type, polynucleotides of the invention can be used as hybridization probes to detect the presence of the particular cell or tissue MRNA using, e.g., in situ hybridization.

The polypeptides according to the invention can be used in a variety of procedures and methods that are currently applied to other proteins. For example, a polypeptide of the invention cane be used to generate an antibody that specifically binds the polypeptide. The polypeptides of the invention also can be used for the study of mechanisms of learning and memory.

Methods are also provided for preventing, treating or ameliorating a medical condition which comprises administering to a mammalian subject a therapeutically effective amount of a composition comprising a protein of the present invention or a polynucleotide of the present invention and a pharmaceutically acceptable carrier. In particular, the polypeptides and polynucleotides of the invention can be utilized, for example, as part of methods for improving learning and memory in normal subjects or to ameliorate learning and memory deficits in impaired subjects. In one embodiment, a polynucleotide of the invention is delivered to a patient in an appropriate vector that directs expression of the polypeptide in neuronal tissue.

The methods of the present invention further relate to the methods for detecting the presence of the polynucleotides or polypeptides of the invention in a sample. Such methods can, for example, be utilized as a prognostic indicator of learning and memory impairment syndromes or deficits in affected subjects.

BRIEF DESCRIPTION OF THE FIGURES

FIGS. 4A–4C Nucleotide (SEQ ID NO: 3) and predicted amino acid sequence of Rbt KKIAMRE kinase (SEQ ID NO: 4). The deduced 566 amino acid sequence of the open reading frame is shown in standard single letter code. Asterisks show the in-frame stop codons in the 5' and 3' untranslated regions. The 207-bp fragment near the 3' end identified by DD-PCR is underlined.

FIGS. 5A–5C Comparison of the predicted amino acid sequences of the cdc2-related kinases and MAP kinases. Dashes indicate residues identical to Rbt KKIAME kinase, dots represent gaps in the sequence to optimize the alignment, and asterisks indicate stop codons. Boxes indicate the region of the conserved PSTAIRE motif in cdc2 used for the kinase nomenclature, as well as the conserved threonine (T) and tyrosine (Y) residues, the regulatory phosphorylation sites required for MAP kinase activation.

FIG. 7. In situ hybridization analysis of KKIAMRE kinase in rabbit brain. (A) A 30 µm coronal section of the cerebellum from a conditioned rabbit showing expression of Rbt KKIAMRE kinase in the granule cell layer, the cerebellar deep nuclei, and brainstem nuclei. (B) Prominent expression of Rbt KKIAMRE kinase is evident in the pyramidal cell layer of the hippocampus and the dentate granule cell layer. Weaker expression is observed in the cerebral cortex. Brain sections were hybridized with an 876-bp $^{35}$S-UTP labeled riboprobe and exposed to film for 14 days. Sections hybridized with the control sense riboprobe showed only background signal.

FIG. 9. Genomic DNA sequence of rbt KKIAMRE kinase (SEQ ID NO: 5).

DETAILED DESCRIPTION OF THE INVENTION

Definitions

Figure 1:
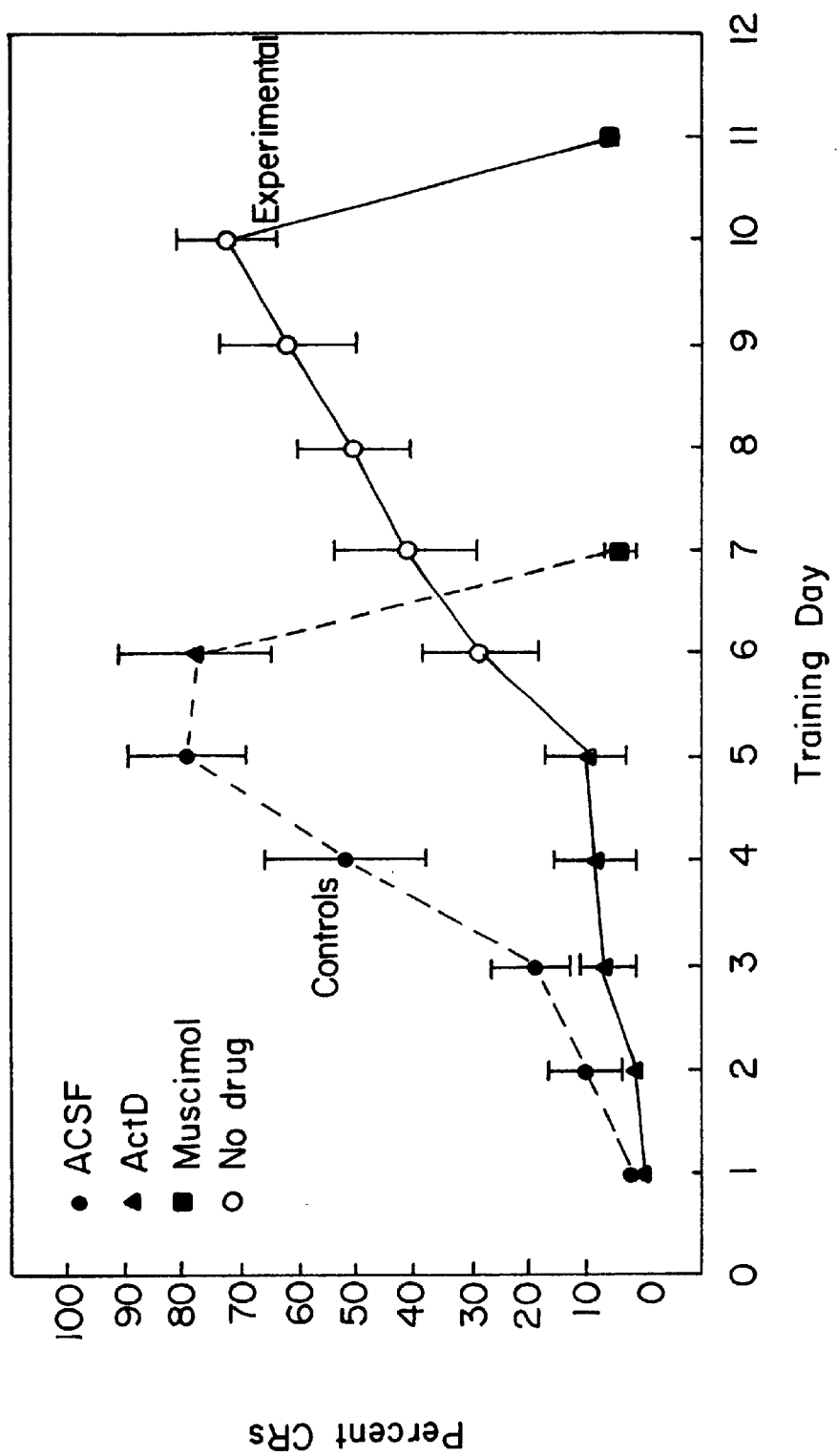
FIG. 1. Infusion of ActD into the IN inhibited eyeblink conditioning. Graph shows average percent CRs for control (n=5) and experimental (n=7) animals. All subjects were trained with only 10 paired CS-US trials per day. The control group (●) received ACSF infusion for the first 5 training days, 1 ng ActD on the 6th training day (▼), and 1 µg muscimol on day 7 (■). The experimental group (▼) received infusion of 1 ng ActD each day for 5 days. After 2 days rest, experimental animals were trained without drug infusion for 5 more days (○). At day 11, the experimental group was infused with 1 µg of muscimol (∪).

The term "nucleotide sequence" refers to a heteropolymer of nucleotides or the sequence of nucleotides. One of skill in the art will readily discern from contextual cues which of the two definitions is appropriate. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment," "portion," or "segment" refer to a stretch of nucleotide residues which is long enough to use in polymerase chain reaction (PCR) or various hybridization procedures to identify or amplify identical or related parts of mRNA or DNA molecules.

"Oligonucleotides" or "nucleic acid probes" refer to polynucleotides that may be prepared based on the polynucleotide sequences provided herein. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than 1 kb. After appropriate testing to eliminate false positives, these probes may, for example, be used to determine whether specific mRNA molecules are present in a cell or tissue.

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989. Molecular Cloning: A Laboratory Manual, Cold Spring Harbor, New York; or Ausubel, F. et al., 1989, Current Protocols in Molecular Biology, John Wiley & Sons, New York, both of which are incorporated herein by reference in their entirety.

The term "recombinant," when used herein to refer to a polypeptide or protein, means that a polypeptide or protein is, derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native, endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "active" refers to those forms of the polypeptide which retain the biologic and/or immunologic activities of any naturally occurring polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 2% (i.e., the number of individual residue substitutions, additions, and/or deletions in a substantially equivalent sequence, as compared to the corresponding reference sequence, divided by the total number of residues in the substantially equivalent sequence is about 0.02 or less). Such a sequence is said to have 98% sequence identity to the listed sequence. In one embodiment, a substantially equivalent, e.g., mutant, sequence of the invention varies from a listed sequence by no more than 2% (98% sequence identity); in a variation of this embodiment, by no more than 0.5% (99.5% sequence identity); and in a further variation of this embodiment, by no more than 0.1% (99.9% sequence identity). Substantially equivalent, e.g., mutant, amino acid sequences according to the invention generally have at least 98% sequence identity with a listed amino acid sequence, whereas substantially equivalent nucleotide sequence of the invention can have lower percent sequence identities, taking into account, for example, the redundancy or degeneracy of the genetic code. For the purposes of determining equivalence, truncation of the mature sequence (e.g., via a mutation which creates a spurious stop codon) should be disregarded.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes that produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

Each of the above terms is meant to encompasses all that is described for each, unless the context dictates otherwise.

Polynucleotides and Nucleic Acids of the Invention

Nucleotide and amino acid sequences of the invention are reported below. The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

Nucleic Acids of the Invention

SEQ ID NOS: 3 and 5 are, respectively, cDNA and genomic DNA sequences that encode the polypeptide sequence of SEQ ID NO: 4.

The proteins of the invention are also useful for making antibody substances that are specifically immunoreactive with KKIAMRE kinase. Antibodies and other small molecules which bind to the protein of the invention can act as blocking agents, or as activators.

In particular embodiments, the isolated polynucleotides of the invention include, but are not limited to, a polynucleotide comprising the nucleotide sequence of SEQ ID NO: 3 and SEQ ID NO: 5.

The polynucleotides of the invention also provide polynucleotides including nucleotide sequences that are substantially equivalent to the polynucleotides recited above. Polynucleotides according to the invention can have at least about 95%, more typically at least about 99%, and even more typically at least about 99.5%, sequence identity to a polynucleotide recited above. The invention also provides the complement of the polynucleotides including a nucleotide sequence that has at least about 95%, more typically at least about 99%, and even more typically at least about 99.5%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, N.Y.). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof; Allelic variations can be routinely determined by comparing the sequence provided in SEQ ID NOS: 3 or 5, representative fragments thereof, or a nucleotide sequence at least 98% identical to SEQ ID NOS: 3 or 5, with a sequence from another isolate. An allelic variation is more typically at least 99% identical to SEQ ID NOS: 3 or 5 and even more typically 99.8% identical to SEQ ID NOS 3 or 5. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS: 3 or 5 or fragments thereof. The recombinant constructs of the present invention comprise a vector, such as a plasmid or viral vector, into which a nucleic acid having the sequence of SEQ ID NOS: 3 or 5 or fragments thereof is inserted, in a forward or reverse orientation. In the case of a vector comprising one of the ORFs of the present invention, the vector may further comprise regulatory sequences, including for example, a promoter, operably linked to the ORF.

Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al., supra. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell that drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran-mediated transfection, or electroporation (Davis, L. et al., *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual*, Second Edition, Cold Spring Harbor, N.Y. (1989), the disclosure of which is hereby incorporated by reference.

Polypeptides of the Invention

The isolated polypeptides of the invention include, but are not limited to, a polypeptide comprising the amino acid sequence of SEQ ID NO: 4. The polypeptides of the invention further include polypeptides which comprise one or more specific domains of the amino acid sequence in SEQ ID NO: 4.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The invention further provides a polypeptide including an amino acid sequence that is substantially equivalent to SEQ ID NO: 4. Polypeptides according to the invention can have at least about 98%, and more typically at least about 99%, and even more typically 99.5 sequence identity to SEQ ID NO: 4.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells that have been altered to express the desired polypeptide or protein. One skilled in the art can readily adapt procedures for introducing and expressing either recombinant or synthetic sequences into eukaryotic or prokaryotic cells in order to generate a cell that produces one of the polypeptides or proteins of the present invention. The purified polypeptides can be used in in vitro binding assays that are well known in the art to identify molecules that bind to the polypeptides.

The protein may also be produced by known conventional chemical synthesis. Methods for constructing the proteins of the present invention by synthetic means are known to those skilled in the art. For polypeptides more than about 100 amino acid residues, a number of smaller peptides will be chemically synthesized and ligated either chemically or enzymatically to provide the desired full-length polypeptide. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences substantially equivalent to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein of the invention may also be expressed in a form that will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein.

The polypeptide sequences encoded by SEQ ID NOS: 3 or 5 have numerous applications in techniques known to those skilled in the art of molecular biology. The polypeptides of the invention and/or their agonists and antagonists are useful in methods for improving learning and memory in normal subjects or to ameliorate learning and memory deficits in impaired subjects. The polypeptides of the invention may also be used to generate antibodies for diagnosis or therapy of such disease states.

Uses and Biological Activity

The polynucleotides and polypeptides of the present invention exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)),to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymnology: Guide to molecular Cloning Techniques", Academic Press, Berger S. L. and A. R. Kimmel eds., 1987.

Gene Therapy

Polynucleotides of the present invention can also be used for gene therapy for the treatment of disorders which are mediated by KKIAMRE kinase. Such therapy would achieve its therapeutic effect by introduction of the appropriate KKIAMRE kinase polynucleotide (e.g., SEQ ID NO: 5) which contains a KKIAMRE kinase genomic sequence (sense), into cells of subjects having learning and memory impairments. Delivery of sense KKIAMRE kinase polynucleotide constructs can be achieved using a recombinant expression vector such as a chimeric virus or a colloidal dispersion system. An expression vector including the KKIAMRE kinase polynucleotide sequence could be introduced into neuronal cells ex vivo, for example, using embryonic neurons or stem cells. The cells are then reintroduced into the subject, (e.g., into subject's brain using sterotactic or radiographically guided surgical methods).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian etrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV), and gibbon ape leukemia virus (GaLV), which provides a broader host range than many of the murine viruses. A number of additional retroviral vectors can incorporate multiple genes. All of these vectors can transfer or incorporate a gene for a selectable marker so that transduced cells can be identified and generated. By inserting KKIAMRE kinase sequence of interest into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences that can be inserted into the retroviral genome to allow target specific retroviral vector containing the KKIAMRE sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines which have deletions of the packaging signal include but are not limited to: PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Antibodies

Another aspect of the invention is an antibody that specifically binds the polypeptide of the invention. Such antibodies can be either monoclonal or polyclonal antibodies, as well as fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies that specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the imunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., *Monoclonal Antibodies Technology: Laboratory Techniques in Biochemistry and Molecular Biology*, Elsevier Science Publishers, Amsterdam, The Netherlands (1984); St. Groth et al., *J. Immunol.* 35:1–21 (1990); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal that is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell that produces an antibody with the desired characteristics. These include screening the hybridomas with an ELISA assay, western blot analysis, or radioimmunoassay (Lutz et al, *Exp. Cell Research*. 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody-containing antiserum is isolated from the immunized animal and is screened for the presence of antibodies with the desired specificity using one of the above-described procedures. The present invention further provides the above-described antibodies in detectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J Immunol. Meth.* 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "*Handbook of Experimental Immunology*" 4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as for immuno-affinity purification of the proteins of the present invention.

Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOS: 3 or 5. Because the corresponding gene is only expressed in a limited number of tissues, especially adult tissues, a hybridization probe derived from SEQ ID NOS: 3 or 5 can be used as an indicator of the presence of RNA of cell type of such a tissue in a sample as shown in Example 3.

Any suitable hybridization technique can be employed, such as, for example, in situ hybridization-PCR as described, U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLES

Example 1

Actinomycin D Reversibly Inhibited Eyeblink Conditioning

Rabbits underwent eyeblink training 30 min. after infusion of 1 ng of actinomycin D (ActD) or artificial cerebrospinal fluid (ACSF) into the dorsal anterior IN ipsilateral to the trained eye. Rabbits were trained with 10 paired tone-air trials per day to insure that ActD could act during learning (see Methods). An ANOVA was completed for the first five days of training for both groups (ACSF and ActD): the groups differed significantly $F_{1,10}=15.4$, $p<0.003$; days of training was significant, $F_{4,40}=17.9$, $p<0.0001$; as was the interaction, $F_{4,40}=14.2$, shown in FIG. 1, rabbits receiving ACSF infusion reached criteria (>80% CR) at the end of five days of training (ANOVA over training days 1–5: $F_{4,16}=19.9$, $p<0.01$). Infusion of ActD at day 6 into these control animals did not prevent expression of acquired CRs. Infusion of 1 μg of muscimol on day 7 completely abolished the CRs (see Krupa et al., 1993). Rabbits receiving ActD infusions exhibited low levels of CRs at the end of five days (ANOVA over training days 1–5: $F_{4,24}=1.35$, ns). After 2 days rest, animals in the experimental group were trained without drug infusion, and they showed a gradual increase of CRs (ANOVA over training days 6–10: $F_{4,24}=7.61$, $p<0.01$). Most animals in the experimental group reached criterion after 5 days of additional training without drug infusion. At day 11, the experimental group was infused with 1 μg of muscimol, which completely abolished the expression of CRs. Cannula placements were all in or within close approximation to the dorsal anterior interpositus nucleus and were effective, as demonstrated by muscimol abolition of the CRs in all animals (Krupa et al., 1993).

Example 2

Identification and Cloning of Rabbit KKIAMRE KINASE

Figure 2:
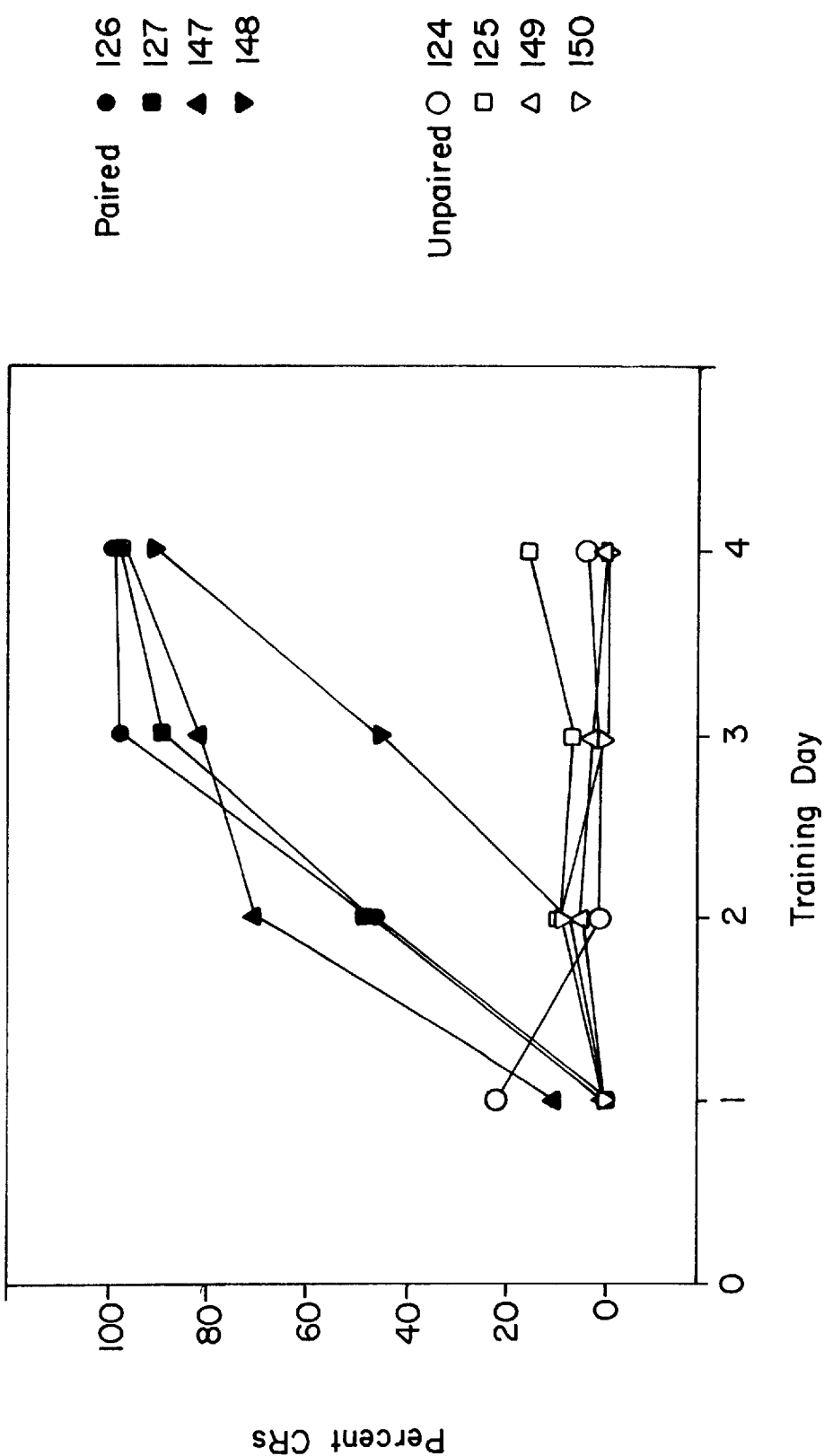
FIG. 2. Learning curves for animals used in DD-PCR analysis. Conditioned animals (closed symbols) were trained with the standard delay procedure (see text), 100 trials per day. Control animals (open symbols) received unpaired CS and US stimuli.
Figure 3:
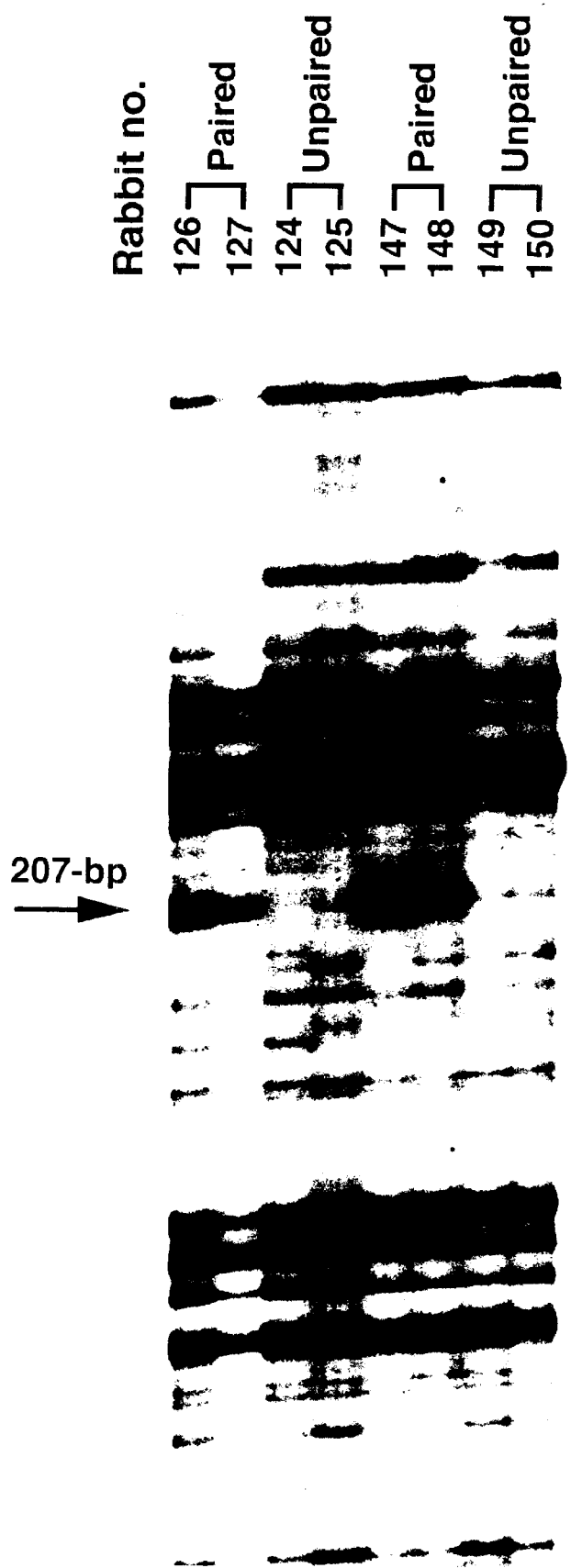
FIG. 3. DD-PCR patterns of RNAs isolated from the cerebellar deep nuclei of CS-US paired and unpaired stimuli conditioned rabbits. Differential display reactions were performed using 5'-AAGCTTTTTTTTTTTA-3' (SEQ ID NO: 1) as an anchored primer and 5'-AAGCTTTGGTCAG-3' (SEQ ID NO: 2) as a random arbitrary primer. The arrow indicates a PCR-amplified 207-bp cDNA fragment that appeared to be induced with paired training.

Four experimental rabbits trained with our standard CS-US paired stimuli schedule (100 trials per day) showed over 80% CRs after 4 days of training, while the four control rabbits trained with unpaired CS-US stimuli did not show a significant level of CRs (FIG. 2). All subjects were sacrificed immediately following the day 4 training session and their brains removed. RNA was isolated from the IN and overlying cortex (region HVI) since these regions represent essential sites for eyeblink conditioning (Thompson and Krupa, 1994). DD-PCR was carried out by using 48 different sets of primers. A 207-bp cDNA fragment was identified that was differentially expressed in the cerebellar deep nuclei (FIG. 3). The nucleotide sequence of this cDNA fragment did not share homology with any other known sequences. Approximately $5\times10^5$ plaques of a λgt11 rabbit brain cDNA library (Clonetech) were screened using the DD-PCR cDNA fragment as the probe and 8 overlapping clones were isolated. Eight additional overlapping clones were isolated by screening with a more 5' region of the cDNA. A full-length cDNA (3080 bp) was constructed from the overlapping clones, and it contains a 1698-bp open reading frame. FIG. 4 shows the nucleotide sequence and predicted amino acid sequence of the cDNA. Comparison of the predicted amino acid sequence of the cDNA with the Genbank database (BLAST fileserver) revealed high homology with human p56 protein kinase (p56 KKIAMRE) which was reported to be related to cdc2 and MAP kinases (Taglienti, et al., 1996). These proteins share 97.2% amino acid identity in the kinase domain (FIG. 5). The molecule we isolated was thus named rabbit KKIAMRE kinase (Rbt KKIAMRE kinase). Although the Rbt KKIAMRE kinase was very similar to that of p56 KKIAMRE, Rbt KKIAMRE kinase had a stretch of extra 77 amino acids near the 3' region. KKIAMRE kinase shares homology with Ser/Thr kinases p42 KKIALRE (Meyerson et al., 1992), cdc2 (Lee and Nurse, 1987), cdk2 (Tsai et al., 1991), and members of the MAP kinase family, ERK1 (Boulton et al., 1990), JNK1 (Derijard et al., 1994), and p38 (Lee et al., 194) (FIG. 5).

Example 3

Regional Expression of Rbt KKIAMRE Kinase

Figure 6:
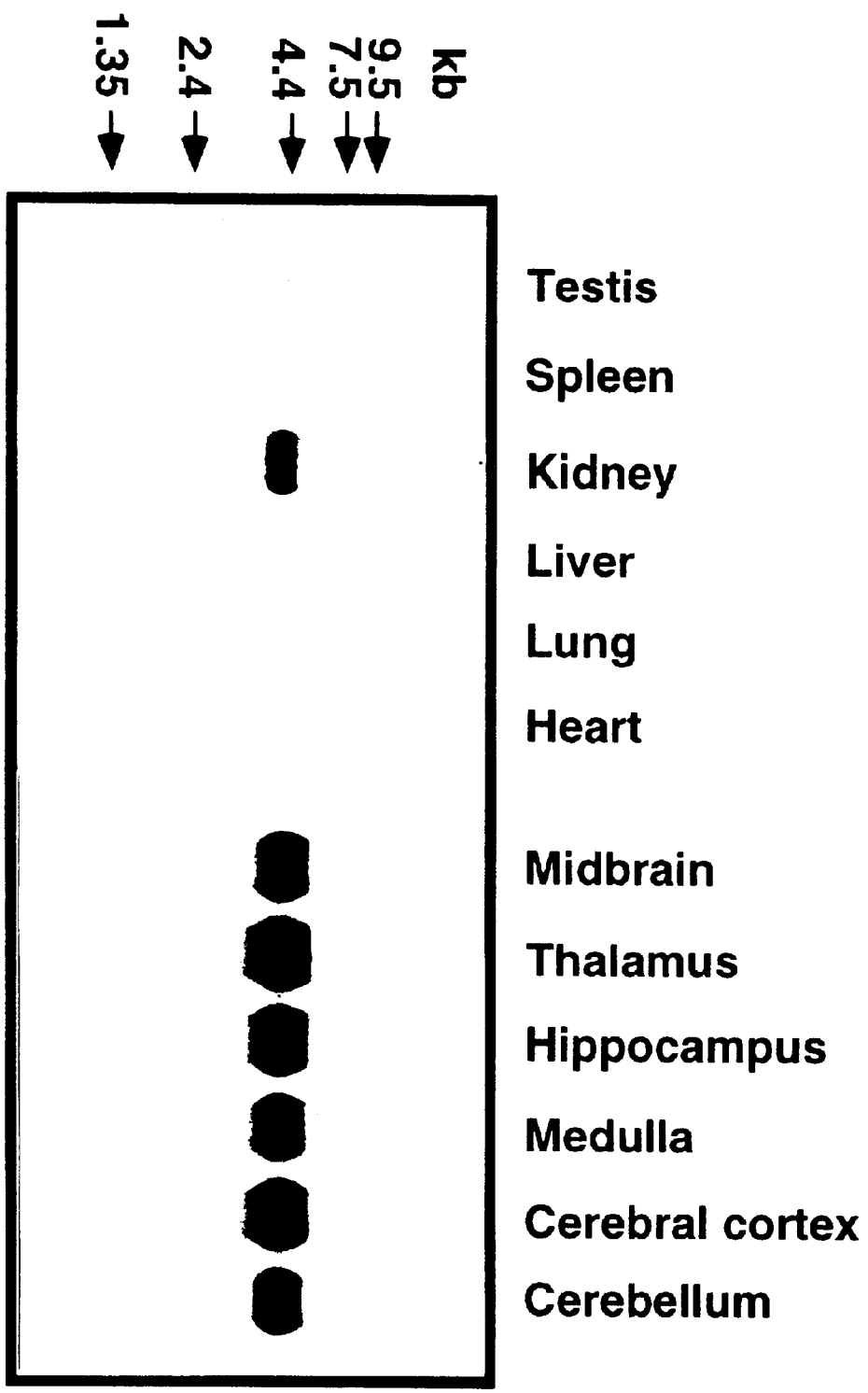
FIG. 6. Northern blot analysis of Rbt KKIAMRE kinase expression in naive rabbit. Three µg of poly(A)+RNA extracted from each brain region and peripheral tissue was hybridized with a 876-bp cDNA fragment in the coding region. Molecular weight standards are indicated by arrows on the left.

The expression pattern of Rbt KKIAMRE kinase MRNA was examined in various tissues and in the brain regions of naive rabbits by Northern blot analysis. Rbt KKIAMRE kinase was expressed predominantly in the brain, but expression was also evident in kidney, lung, and testis (FIG. 6). The tissue-specific expression pattern of Rbt KKIAMRE kinase was thus similar to that of p56 KKIAMRE (Taglienti et al., 1996). For the Rbt KKIAMRE kinase, Northern blot revealed a single transcript of approximately 4 kb in each tissue (FIG. 6), whereas two major transcripts were observed in adult testis and kidney for p56 KKIAMRE (Taglienti et al., 1996). In situ hybridization using an 876-bp riboprobe showed that the KKIAMRE kinase was expressed mainly in the cerebellum, the brainstem, and the hippocampus of naive rabbits. A two-week exposure time was required to achieve a modest signal on β-max film (Amersham). Within the cerebellum, expression was seen in the granule cell layer as well as the deep cerebellar nuclei (FIG. 7A). KKIAMRE kinase was also expressed in several brainstem nuclei, in particular the vestibular and facial nuclei. Prominent expression was evident in the pyramidal cell layer of the hippocampus, and to a lesser extent the dentate granular layer (FIG. 7B). Weaker expression was also observed in the cerebral cortex.

Example 4

Conditioning-dependent Induction of Rbt KKIAMRE Kinase in the IN

Figure 8:
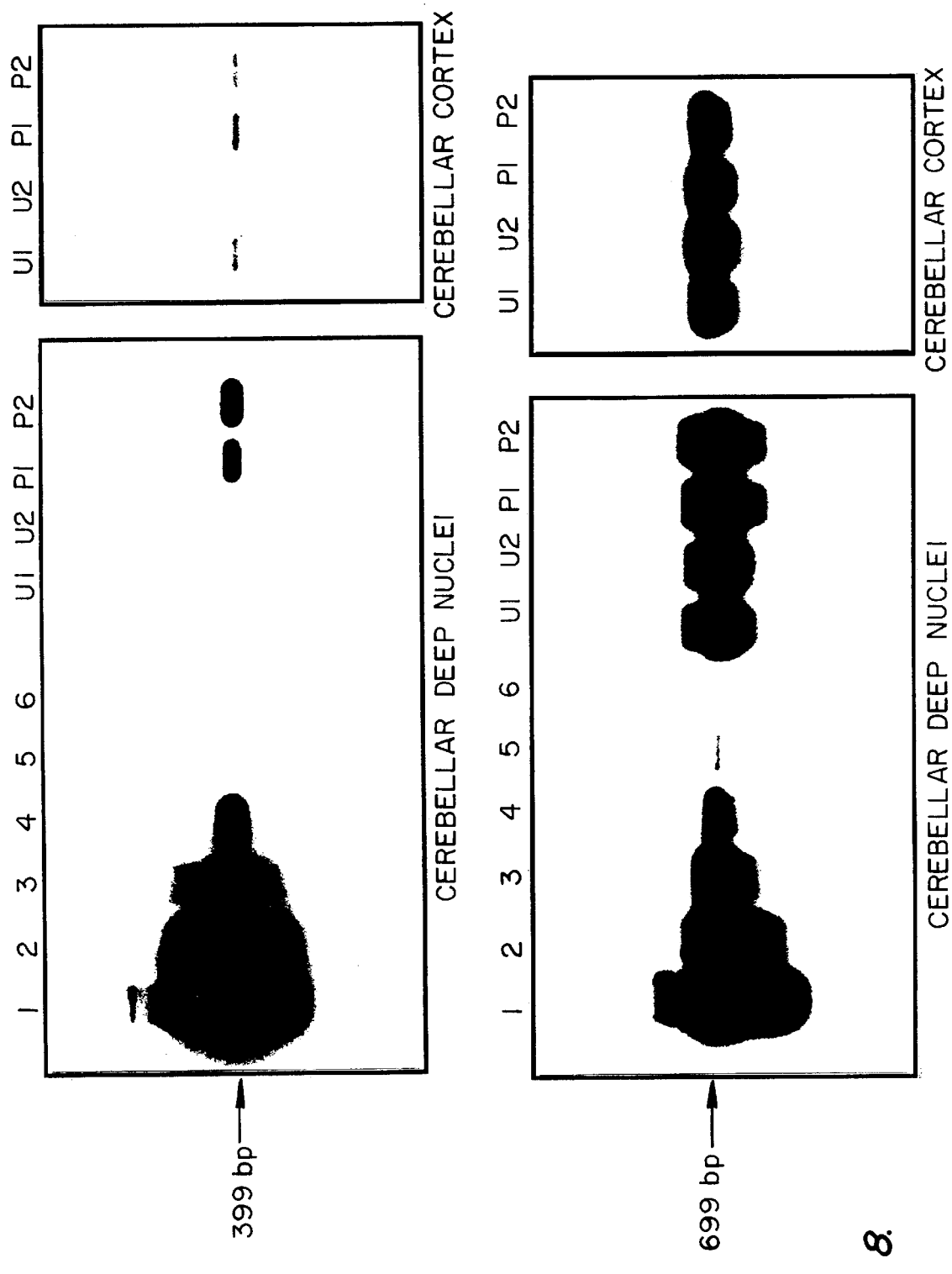
FIG. 8. RT-PCR/Southern blot analysis of gene expression in eyeblink conditioned rabbit. (A) Expression of Rbt KKIAMRE kinase in the cerebellar deep nuclei and cerebellar cortex. A 399-bp RT-PCR product was hybridized with a 677-bp cDNA fragment in the 3' non-coding region. Lanes U1 and U2 represent RNA from rabbits trained with unpaired stimuli and P1 and P2 RNA from well-conditioned rabbits. For semi-quantitative analysis, serial dilutions of the control cDNA plasmid was used for PCR: $2\times10^6$ copies (lane 1), $2\times10^5$ copies (lane 2), $2\times10^4$ copies (lane 3), $2\times10^3$ copies (lane 4), $2\times10^2$ copies (lane 5), and $2\times1$ (lane 6). PCR was performed for 30 cycles. (B) Expression of a control gene NF-L using the same RNA samples as in (A). A 699-bp fragment was amplified from 27 PCR cycles and hybridized with a 855-bp cDNA probe in the coding region. Copy number of plasmids used for positive control PCR (lanes 1–6) was the same as mentioned above.

Previous studies indicate that cerebellar cortex and IN are both involved in eyeblink conditioning. To determine the site where the Rbt KKIAMRE kinase may participate in eyeblink conditioning, we examined the level of transcripts of the Rbt KKIAMRE kinase in these tissues of the eyeblink conditioned animals (100 trials/day; 4 days) by a semi-quantitative RT-PCR/Southern blot analysis. RNAs isolated from the left cerebellar deep nuclei and cerebellar cortex were reverse transcribed using oligo (dT) primer and PCR was performed with primer sets designed for Rbt KKI-AMRE kinase and rabbit neurofilament-L (NF-L) cDNAs. To confirm conditioning-induced expression initially found by 207 bp fragment, a part of KKIAMRE kinase mRNA outside of the 207-bp fragment was amplified by PCR. As shown in FIG. 8 above, cerebellar deep nuclei from animals trained with CS-US paired stimuli (lanes P1 and P2) showed nearly 10 times increased expression of Rbt KKIAMRE kinase when compared to those of animals trained with unpaired stimuli (lanes U1 and U2). However, no difference in expression was observed in the cerebellar cortex between these two groups. PCR with NF-L primers using the same cDNA templates showed comparable levels of NF-L expression in the deep nuclei and cortex of both trained and unpaired pseudo-trained animals (FIG. 8 below). These results indicated that the increased expression of Rbt KKI-AMRE kinase in the brain was specific for conditioned animals, and that the increased expression was localized to the cerebellar deep nuclei.

Example 5

Associative Motor Learning Requires New RNA Synthesis

Our results show that infusion of ActD, an RNA synthesis inhibitor, into the cerebellar interpositus nucleus over the course of eyeblink conditioning completely prevents learning, consistent with a report that protein synthesis inhibition in this nucleus interfered with eyeblink conditioning (Bracha and Bloedel 1996). The present results thus strongly support the idea that associative motor learning requires new RNA synthesis. Since eyeblink conditioning typically requires many trials over several days, it is a learning paradigm apparently lacking an obvious short-term component. In addition, once a rabbit is well-trained, the CR is robust, not easily extinguished and is retained for months (Lavond et al., 1984). Indeed, acquisition of the conditioned NM response shows similar temporal characteristics to those found in other associative learning tasks where formation of long-term memory is required. This is consistent with the idea that long term memory requires long lasting changes in synaptic efficacy, which most likely requires synthesis of new RNA/proteins. Accordingly, infusion of ActD into the interpositus nucleus inhibited eyeblink conditioning. However, once the animal was conditioned, infusion of ActD had no effect on the performance of CRs. Thus, new mRNA synthesis is essential for acquisition but not expression of the learned response. These results further support our hypothesis that eyeblink conditioning involves long term changes in the synapses within the cerebellar interpositus nucleus. In the following experiments we attempt to determine the mRNA that is expressed in the interpositus nucleus during conditioning.

Example 6

Eyeblink Conditioning Induces a Cdc2-related Kinase in the Brain

Differential display analysis indicated that eyeblink conditioning led to an increased expression of KKIAMRE kinase, a cdc2-related kinase, in the cells of deep cerebellar nuclei. The amino acid motif KKIAMRE, like the KKI-ALRE motif, is a highly conserved motif related to PSTAIRE of the cyclin dependent kinases (Meyerson et al., 1992). The Thr-Xaa-Tyr (Thr-Asp-Tyr in the case of KKI-AMRE and KKIALRE) phosphorylation motif, which is required for MAP kinase activation and regulated by the upstream dual-specificity kinases (Nishida and Gotoh, 1993), is conserved in the region between protein kinase subdomains VII and VIII of Rbt KKIAMRE kinase.

Our result raises interesting questions since cdc2 and MAP kinases are primarily involved in cell cycle regulation.

Since neurons in the mammalian brain are post-mitotic, these kinases may serve a different function in the brain. Recent reports described a neuronal cdc2-like kinase, cdk5, together with a p25 regulatory subunit, which could phosphorylateneurofilament and tau proteins and may be involved in neuronal sprouting and development (Lew and Wang, 1995; Tang et al., 1996). An attractive hypothesis is that induction of KKIAMRE kinase may be a signal for cellular growth, which would lead to dendritic branching or extension of processes. Such long-lasting synaptic changes would be suitable for the establishment of a long-term memory trace. Hence, KKIAMRE kinase, like Cdk5, may belong to a novel family of kinases that play a critical role in cognitive functions of the brain.

Another subgroup of this kinase family (FIG. 5), the MAP kinase, was reported to be implicated in a signal transduction pathway that controls long-term synaptic facilitation (LTF) in Aplysia (Martin et al., 1997; Bailey et al., 1997). MAP kinase possibly regulates LTF by phosphorylation of transcription factors such as Aplysia homologs of cyclic AMP responsive element-binding proteins (CREBs), CREB1, CREB2 and C/EBPb in the nucleus, as well as by phosphorylation of apCAM (Aplysia neural cell adhesion molecule homolog) in the synaptic vicinity. Furthermore, p42, a MAP kinase isoform, was reported to be activated in the CA1 area following stimuli which induced long term potentiation (LTP) in rat hippocampal slices (English and Sweatt, 1996). These observations suggest that MAP kinases are important regulators of synaptic plasticity in neurons. Thus, if Rbt KKIAMRE kinase functions in the same way as MAP kinases, then KKIAMRE kinase plays a role in long term synaptic changes that may underlie memory consolidation in the brain.

Other types of kinases in the brain have been shown to play an essential role in different learning paradigms. Much recent attention has been given to the $Ca2^+$-calmodulin dependent protein kinase II, which has been shown to be necessary for hippocampal LTP as well as spatial learning tasks (Silva et al., 1992; Soderling, 1993; Mayford et al., 1996; Barria et al., 1997). Similarly, the cAMP-dependent protein kinase pathway and the associated molecule CREB has been implicated in long term memory in several animal models of associative learning (Kaang et al., 1993; Bourtchuladze et al., 1994; Yin et al., 1994; Abel et al., 1997). Protein kinase C has been demonstrated to play an important role in hippocampal LTP (Abeliovich et al., 1993; Leahy et al., 1993; Wang and Feng, 1992) as well as cerebellar LTD (Crepel and Krupa, 1988; Linden and Connor, 1991), two proposed neural mechanisms underlying associative learning in animals. Since Rbt KKIAMRE kinase is expressed in the hippocampal pyramidal cell layer, its function may also be important in hippocampal-dependent learning such as spatial learning.

Although the protein/gene structure of Rbt KKIAMRE kinase is a homolog of human KKIALRE, its cellular function may be different from that of human. The cellular distribution of KKIALRE protein in the human brain was shown with antibodies to the C-terminal subregion (Yen et al., 1995). KKIALRE was present in fibrous astrocytes in the white matter, perivascular and subpial spaces, as well as Bergmann glia in the cerebellum, but not in neurons. In contrast, the Rbt KKIAMRE seems to be expressed in neurons, as evidenced by in situ hybridization (FIG. 7)., This difference implies multiple roles of this kinase in the brain. Further work will be required to uncover the role of Rbt KKIAMRE and its signaling pathway in associative motor learning as well as other types of associative learning tasks.

Although we have shown that new mRNA synthesis is required for conditioning and KKIAMRE is expressed during conditioning, it is still not clear whether KKIAMRE is necessary for the acquisition of conditioning. Disruption of the Rbt-KKIAMRE gene in mice would further clarify the link between this kinase function in the brain and behavior.

Example 7

Experimental Procedures 7.1 Subjects

New Zealand White male rabbits (Oryctolagus cuniculus), weighing between 2 and 3 kg were individually housed at the University of Southern California Hedco Neuroscience Building vivariunm with a 12-hr light and dark cycle. The experiment was conducted during the light phase of the cycle. Rabbits had ad lib access to food and water.

7.2 Infusion of Actinomycin D

Stainless steel guide cannulas (25 ga) were implanted in the head of the animals with the tip fixed at 1.5 to 2.0 mm dorsal to the IN ipsilateral to the eye to be trained (left) (stereotaxic coordinates from lambda: 0.8 mm anterior, 5.2 mm lateral, and 14.0 mm ventral). Each guide cannula was filled with an inner stainless steel stylet designed to keep the guide cannula patent. Animals were given 5 days to recover from surgery. At infusion the stylet was removed and an inner cannula (31 ga) was inserted to the target locus. Delivery of fluids through the inner cannula was accomplished by a 10 μl Hamilton syringe driven by a syringe pump. Fluids were delivered to the target area at a rate of 0.38 μl per min for 2.6 min. For the experimental group, 1 ng of ActD (in 1 μl of vehicle) was infused daily 30 min prior to the start of each training session for 5 days (n=7). This dosage was determined in pilot studies; higher doses, e.g. 5 ng, caused permanent damage to the tissue. The animals were given 2 days rest and then trained for 5 more days without drug infusion. At training day 11, the experimental group was treated with 1 μg muscimol which is known to reversibly inactivate the IN (Krupa and Thompson, 1997). For the control group, 1 μl of ACSF (vehicle) was infused into the IN for 5 days (n=5). At day 6, control animals were infused with 1 ng of ActD 30 min prior to training. On training day 7, 1 μg of muscimol was infused.

7.3 Behavioral Training

For the infusion experiments, all animals were subjected to eye-blink conditioning under the delay paradigm. The rabbits were allowed one day (1 hour) of habituation to the restrainer and the behavioral recording chamber. On the following day, paired tone-airpuff training began. For each day, the training session began 30 min post drug infusion and we gave only 10 trials/day (instead of the standard 100 trials per day, see below) in order to maximize the possibility that ActD was acting on the learning process before the long term memory had been well established. The tone CS was a 350 ms, 1000 Hz., 85 dB tone and the airpuff US was a 100 ms puff of air (3 psi at the source) delivered to the rabbit's cornea, the CS and US coterminating. The mean intertrial interval (ITI) was 60±10 sec. Nictitating membrane (NNI) conditioned responses (CRs) were measured using a mini-torque potentiometer attached to a small loop of monofilament nylon thread on the NM of the rabbit's left, eye. Output of the potentiometer was digitized and recorded by computer. A conditioned response was defined as any NM extension response greater than 0.5 mm that occurred after tone onset but before airpuff onset. The intra- and intertrial timing, stimulus presentations, data collection and analysis were performed by a PC with a program written in Forth and machine language (Lavond and Steinmetz, 1989b).

For DD-PCR analysis, 4 animals in the experimental group were trained under the standard delay paradigm where each daily training session consisted of 100 trials arranged into 10 blocks. Each block included 1 CS-alone, 1 US-alone, and 8 CS-US paired trials. The intertrial interval (ITI) was 30±10 sec. The four animals in the control group were given an equal number of unpaired tone and air-puff stimuli.

7.4 RNA Isolation and Differential Display

Once the paired group reach criteria (showing>80% CR), all animals were sacrificed by lethal injection with sodium pentobarbital (300 mg i.v.) through the ear vein and the brains were quickly removed and frozen. The cerebellum was then mounted on a cryostat and cut in the coronal plane until the deep nuclei just became visible. The deep nuclei tissue was removed and homogenized in TRIzol Reagent (GIBCO/BRL). RNA was isolated following manufacturer's protocol. RNA samples were treated with RQ1 RNase-free DNase (Promega) to remove chromosomal DNA.

Differential display was performed following the protocol of RNA Image kit (GenHunter). Two-hundred ng of total RNA was used for reverse transcription followed by arbitrarily primed PCR using $\alpha$-[$^{32}$P]dATP (2,000 Ci/mmole, Amersham) and Taq DNA polymerase (Promega). Samples were then separated by electrophoresis on 6% polyacrylamide sequencing gels. The gels were dried under vacuum and exposed to X-ray films. DNA from the band of interest was extracted and reamplified by PCR following manufacturer's instruction. The amplified DNA fragment was subcloned into the pCR-II vector of the TA Cloning System (Invitrogen). Multiple plasmid preparations were analyzed by EcoRI digestion, 1.5% agarose gel electrophoresis, and DNA sequencing using the Ladderman Sequence kit (TAKARA).

7.5 Probe Labeling and cDNA Library Screening

Plasmid DNA was digested with EcoRI, and the insert was separated from the vector by electrophoresis on 1.2% agarose. The insert band was excised from the gel and purified using the MERMAID kit (BIO 101). Twenty-five ng of the insert was radiolabeled with $\alpha$-[$^{32}$P]dCTP and Megaprime DNA Labeling System (Amersham). Approximately $5\times10^5$ plaques of rabbit brain 5'-Stretch Plus $\lambda$gt11 cDNA library (Clonetech) were screened using the differential display cDNA fragment. The isolated phage clones were purified, digested with EcoRI, and subcloned into Bluescript II vector (Stratagene). Screening of the cDNA library was repeatedly performed using the appropriate probes prepared from primarily isolated cDNA clones. Following identification and sequencing of the cDNA clone encoding rbt KKIAMRE kinase, a rabbit genomic DNA library was screened to locate the clone(s) containing the corresponding genomic sequence for rbt KKIAMRE kinase.

7.6 Northern Blot Analysis

Poly(A)+RNA was purified from total RNA using PolyATract mRNA Isolation Systems (Promega). Denaturedh RNA samples (3 $\mu$g) were subjected to electrophoresis in 1.0% agarose-formaldehyde gels, transferred to GeneScreen Plus hybridization transfer membranes (DuPont/NEN), crosslinked by UV irradiation, and hybridized with a $^{32}$P-labeled cDNA probe. Membranes were exposed to X-ray film at -70° C. with an intensifying screen.

7.7 RT-PCR and Southern Blot Analysis

Two hundred ng of DNase-treated total RNA was reverse transcribed in a 20 $\mu$l reaction mixture with the following composition: 5xRT-buffer (GIBCO/BRL), 10 mM DTT, 0.5 mM dNTPs, 100 nM oligo(dT)12-18 primer (GIBCO/BRL), 40 U of RNasin ribonuclease inhibitor (Promega) and 200 U of MMLV-reverse transcriptase (GIBCO/BRL). After 60 min at 37° C., the reaction was terminated by heating at 95° C. for 5 min and stored at -20° C. PCR amplification was performed for 20 to 35 cycles with the following thermocycle: 30 sec at 94° C., 1 min at 60° C. and 1 min at 72° C. using a GeneAmp PCR System 9600 (Perkin-Elmer). The 20 $\mu$l reaction mixture contained 0.5 U Taq DNA polymerase, 2 $\mu$l of RT mixture, 250 mM dNTPs, 2.0 $\mu$M MgCl+$_2$ and 250 nM each primer. The amplified DNA was separated by agarose gel electrophoresis and transferred to GeneScreen Plus hybridization membrane. The filters were hybridized with a $^{32}$P-labeled cDNA probe. To evaluate gene expression level, the cloned cDNA of the desired sequence were serially diluted ($2\times10^6$ to $2\times10^1$ copies) and processed in the exact manner as the other samples. PCR primers were: (5') TTGCAGAAGAAGGAACGACA (3') (SEQ ID NO: 6) for the sense primer and (5') TGTCGTTCCTTCTTCTG-CAA (3') (SEQ ID NO: 7) for the antisense primer to generate a 399-bp (nucleotide nos. 1846–2244 of Rbt KKI-AMRE kinase). As an internal control for the quality of RNA and RT samples, the rabbit neurofilament-L (NF-L) cDNA (nucleotides no. 948–1646; Soppet et al., 1991) was amplified using the sense primer (5') AAGGCCAAGACCCTG-GAGAT (3') (SEQ ID NO: 8) and the antisense primer (5') TCAATCTTTCTTCTTGGTTG (3') (SEQ ID NO: 9).

7.8 In Situ Hybridization

The procedure was based on Simmons et al. (1989) with slight modifications. Subjects were deeply anaesthetized with sodium pentobarbital and perfused with 500 ml 0.9% saline through the ascending aorta followed by 500 ml 4% ice cold paraforinaldehyde in phosphate-buffered saline. Brains were removed and placed in 10% sucrose and 4% parafornaldehyde for 24 hrs at 4° C. Brains were cut frozen in a cryostat and 30 $\mu$m coronal sections were collected onto gelatin and poly-L-lysine coated slides. Sections were treated with 0.001% proteinase K at 37° C. for 30 min and then acetylated in 0.25% acetic anhydride for 10 min.

An 876-bp fragment of the KKIAMRE kinase cDNA in Bluescript-II vector (Strategene) was used for in vitro transcription. Antisense probe was synthesized from the T3 promoter and control sense probe from T7 promoter using the In Vitro Transcription System (Promega). The probes were labeled with $^{35}$S-UTP to a specific activity of $8\times10_8$ cpm/$\mu$g. Sections were hybridized in 80 $\mu$l of hybridization solution (50% formamide, 5% dextran sulfate, 0.3 M NaCl, 1xDenhardt's solution, 10 mM Tris, pH 8.0, 1 mM EDTA, 0.5 mg/ml tRNA, 10 mM DTT, and $5\times10^6$ cpm/ml of riboprobe). Sections were coverslipped and sealed with DPX resin. Hybridization was carried out at 62° C. for 18 hrs. Post-hybridization washes consisted of several washes in 4xSSC at 25° C. followed by RNase A digestion at 37° C. for 30 min. Stringency of washes was increased gradually with a final wash at 0.5xSSC at 65° C. for 20 min. Slides were dehydrated in ethanol and dried under vacuum. Sections were exposed to $\beta$-max film (Amersharn) for 14 days.

All references in this application to publications, patents, and patent applications are incorporated herein by reference in their entirety.

References

Abel, T., Nguyen, P. V., Barad, M., Deuel, T. A., and Kandel, E. R. (1997). Genetic demonstration of a role for PKA in the late phase of LTP and in hippocampus-based long-term memory. *Cell* 88, 615–626.

Abeliovich, A., Paylor, R., Chen, C., Goda, Y., Silva A. J., Stevens, C. F., and Tonegawa, S. (1993). Modified hippocampal long-tern potentiation in PKC gamma-mutant mice. *Cell* 75, 1253–1262.

Agranoff, B. W. (1967). Memory and protein synthesis. *Scientific American* 216, 115–122.

Aiba, A., Kano, M., Chen, C., Stanton, M. E., Fox, G. D., Herrup, K., Zwingmann, T. A. and Tonegawa, S. (1994). Deficient cerebellar long-term depression and impaired motor learning in mGluR1 mutant mice. *Cell* 79, 377–388.

Bailey, C. H., Kaanga, B.-K., Chen, M., Martin, K. C., Lim, C.-S., Cassadio, A. and Kandel, E. R. (1997). Mutation in the phosphorylation sites of MAP kinase blocks learning-related internalization of apCAM in Aplysia sensory neurons. *Neuron* 18, 913–924.

Barondes, S. H. and Cohen, H. D. (1966). Puromycin effect on successive phases of memory. *Science* 151, 594–595.

Barria, A., Muller, D., Derkach, V., Griffith, L. C., and Soderling, T. R. (1997). Regulatory phosphorylation of AMPA-type glutamate receptors by CAM-KII during long-term potentiation. *Science* 276, 2042–2045.

Boulton, T. G., Yancopoulos, G. D., Gregory, J. S., Slaughter, C., Moomaw, C., Hsu, J. and Cobb, M. H. (1990). An insulin-stimulated protein kinase similar to yeast kinases involved in cell cycle control. *Science* 249, 64–67.

Bourtchuladze, R., Frenguelli, B., Blendy, J., Cioffi, D., Schutz, G., and Silva, A. J. (1994). Deficient long-term memory in mice with a targeted mutation of the cAMP-responsive element-binding protein. *Cell* 79, 59–68.

Bracha, V. and Bloedel, J. R. (1996). The multiple-pathway model of circuits subserving the classical conditioning of withdrawal reflexes. In *The Acquisition of Motor Behavior in Vertebrates* (Bloedel, J. R., Ebner, T. J. and Wise, S. P., eds.), pp. 175–204, MIT Press.

Chen, L., Bao, S., Lockard, J. M., Kim, J. J. and Thompson, R. F. (1996). Impaired classical eyeblink conditioning in cerebellar-lesioned and Purkinje cell degeneration (pcd) mutant mice. *J. Neurosci.* 16, 2829–2838.

Clark, R. E. and Lavond, D. G. (1993). Reversible lesions of the red nucleus during acquisition and retention of a classically conditioned behavior in rabbit. *Behavioral Neuroscience* 107: 264–270.

Clark, R. E., Zhang, A. A. and Lavond, D. G. (1992). Reversible lesions of the cerebellar interpositus nucleus during acquisition and retention of a classically conditioned behavior. *Behavioral Neuroscience* 106: 879–888.

Crepel, F. and Krupa, M. (1988). Activation of protein kinase C induces a long-term depression of glutamate sensitivity of cerebellar Purkinje cells. An in vitro study. *Brain Res.* 458, 397–401.

Davis, H. P. and Squire, L. R. (1984). Protein synthesis and memory. A review. *Psychol. Bull.* 96, 518–559.

Derijard, B., Hibi, M., Wu, I.-H., Barrett, T., Su, B., Deng, T., Karin, M. and Davis, R. J. (1994). JNK1: a protein kinase stimulated by UV light and Ha-Ras that binds and phosphorylates the c-Jun activation domain. *Cell* 76, 1025–1037.

English, J. D. and Sweatt, J. D. (1996). Activation of p42 mitogen-activated protein kinase in hippocampal long term potentiation. *J. Biol. Chem.* 271, 24329–24332.

Ito, M. (1989). Long-term depression. *Annual Review of Neuroscience* 12, 85–102.

Ivkovich, D., Lockard, J. M. and Thompson, R. F. (1993). Interpositus lesion abolition of the eyeblink CR is not due to effects on performance. *Behavioral Neuroscience* 107, 530–532.

Kaang, B. K., Kandel, E. R., and Grant, S. G. (1993). Activation of cAMP-responsive genes by stimuli that produce long-term facilitation in Aplysia sensory neurons. *Neuron* 10, 427–35.

Kim, J. J., Chen, L., Bao, S., Sun, W., and Thompson, R. F. (1996). Genetic dissections of the cerebellar circuitry involved in classical eyeblink conditioning. In *Gene Targeting and New Developments in Neurobiology* (S. Nakanishi et al., eds.) pp. 3–15, Japan Scientific Societies Press.

Krupa, D. J., Thompson, J. K., and Thompson, R. F. (1993). Localization of a memory trace in the mammalian brain. *Science* 260, 989–991.

Krupa, D. J. and Thompson, R. F. (1995). Inactivation of the superior cerebellar peduncle blocks expression but not acquisition of the rabbit's classically conditioned eyeblink response. *Proc Natl Acad Sci USA* 92, 5097–5101.

Krupa, D. J. and Thompson, R. F. (1997). Reversible inactivation of the cerebellar interpositus nucleus completely prevents acquisition of the classically conditioned eyeblink response. *Learning and Memory* 3, 545–556.

Lavond, D. G. and Steinmetz, J. E. (1989a). Acquisition of classical conditioning without cerebellar cortex. *Behav. Brain Res.* 33, 113–164.

Lavond, D. G. and Steinmetz, J. E. (1989b). An inexpensive interface for IBM PC/XT and compatibles. *Behavorial Research Methods, Instruments and Computers* 21, 435–440.

Lavond, D. G., J. S., McCormick, D. A. and Thompson, R. F. (1984). Nonrecoverable learning deficit. *Physiological Psychology* 12, 103–110.

Lavond, D. G., Steinmetz, J. E., Yokaitis, M. H. and Thompson, R. F. (1987). Reacquisition of classical conditioning after removal of cerebellar cortex. *Exp. Brain Res.* 67, 569–593.

Leahy, J. C., Luo, Y., Kent, C. S., Meiri, K. F., Vellano, M. L. (1993). Demonstration of presynaptic protein kinase C activation following long-term potentiation in rat hippocampal slices. *Neurosi.* 52, 563–574.

Lee, J. C., Laydon, J. T., McDonnell, P. C., Gallagher, T. F., Kumar, S., Green, D., McNulty, D., Blumenthal, M. J., Heys, J. R., Landvatter, S. W., Strickler, J. E., McLaughlin, M. M., Siemens, I. R., Fisher, S. M., Livi, G. P., White, J. R., Adams, J. L. and Young, P. R. (1994). A protein kinase involved in the regulation of inflammatory cytokine biosynthesis. *Nature* 372, 739–746.

Lee, M. G. and Nurse, P. (1987). Complementation used to clone a human homolog of the fission yeast cell cycle control gene cdc2. *Nature* 327, 31–35.

Lew, J. and Wang, J. H. (1995). Neuronal cdc2-like kinase. *Trends Biochem. Sci.* 20. 33–37.

Liang, P. and Pardee, A. B. (1992). Differential display of eukaryotic messenger RNA by means of polymerase chain reaction. *Science* 257, 967–971.

Lincoln, J. S., McCormick, D. A. and Thompson, R. F. (1982). Ipsilateral cerebellar lesions prevent learning of the classically conditioned nictitating membrane/eyelid response. *Brain Res.* 242, 190–193.

Linden, D. J. and Connor, J. A. (1991). Participation of postsynaptic PKC in cerebellar long-term depression in culture. *Science* 254, 1656–1659.

Linden, D. J. and Connor, J. A. (1995). Long-term synaptic depression. *Annual Rev: Neurosci.* 18, 319–57.

Martin, K. C., Michael, D., Rose, J. C., Barad, M., Casadio, A., Zhu, H. and Kandel, E. R. (1997). MAP kinase translocates into the nucleus of the presynaptic cell and is required for long-term facilitation in Aplysia. *Neuron* 18, 899–912.

Mayford, M., Bach, M. E., Huang, Y. Y., Wang, L., Hawkins, R. D., and Kandel, E. R. (1996). Control of memory formation through regulated expression of a CaMKII transgene. *Science* 274, 1678–1683.

McCormick, D. A., Clark, G. A., Lavond, D. G. and Thompson, R. F. (1982). Initial localization of the memory trace for a basic form of learning. *Proc. Natl. Acad. Sci. USA* 79, 2731–2735.

Meyerson, M., Enders, G. H., Wu, C.-L., Su, L.-K., Gorka, C., Nelson, C., Harlow, E., and Tsai, L.-H. (1992). A family of human cdc2-related protein kinases. *EMBO J.* 11, 2909–2917.

Montarolo, P. G., Goelet, P., Castellucci, V. F., Morgan, J., Kandel, E. R., and Schacher, S. (1986). A critical period for macromolecular synthesis in long-term heterosynaptic facilitation in Aplysia. *Science* 234, 1249–1254.

Nishida, E. and Gotoh, Y. (1993). The MAP kinase cascade is essential for diverse signal transduction pathways. *Trends Biochem. Sci.* 18, 128–131.

Nordholm, A. F., Thompson, J. K., Dersarkissian, C., and Thompson, R. F. (1993). Lidocaine infusion in a critical region of cerebellum completely prevents learning of the conditioned eyeblink response. *Behav. Neurosci.* 107, 882–886.

Shibuki, K., Gomi, H., Chen, L., Bao, S., Kim, J. J., Wakatsuki, H., Fujisaki, T., Fujimoto, K., Katoh, A., Ikeda, T., Chen, C., Thompson, R. F. and Itohara, S. (1996). Deficient cerebellar long-term depression, impaired eyeblink conditioning, and normal motor coordination in GFAP mutant mice. *Neuron* 16, 587–599.

Silva, A. J., Paylor, R., Wehner, J. M., and Tonegawa, S. (1992). Impaired spatial learning in alpha-calcium-calmodulin kinase II mutant mice. *Science* 257, 206–211.

Simmons, D. M., Arriza, J. L., Swanson, L. W. (1989). A complete protocol for in situ hybridization of messenger RNAs in brain and other tissues with radio-labeled single-stranded RNA probes. *J. Histotech.* 12, 169–181.

Soderling, T. R. (1993). Calcium/calmodulin-dependent protein kinase II: role in learning and memory. *Mol. Cell Biochem.* 127–128,93–101.

Soppet, D. R., Beasley, L. L. and Willard, M. B. (1991). Sequence of the rabbit neurofilament protein. *L. J. Neurosci. Res.* 30, 42–46.

Steinmetz, J. E., Lavond, D. G., Ivkovich, D., Logan, C. G. and Thompson, R. F. (1992). Disruption of classical eyelid conditioning after cerebellar lesions: damage to a memory trace system or a simple performance deficit? *J. Neurosci.* 12, 4403–4426.

Taglienti, C. A., Wysk, M. and Davis, R. J. (1996). Molecular cloning of the epidermal growth factor-stimulated protein kinase p56 KKIAMRE. *Oncogene* 13, 2563–2574.

Tang, D., Lee, K. Y., Qi, Z., Matsuura, I., and Wang, J. H. (1996). Neuronal Cdc2-like kinase: from cell cycle to neuronal function. *Biochem. Cell Biol.* 74, 419–29.

Thompson, R. F. and Krupa, D. J. (1994). Organization of memory traces in the mammalian brain. *Ann. Rev. Neurosci.* 17, 519–549.

Thompson, R. F. (1986). The neurobiology of learning and memory. *Science* 233, 941–947.

Thompson, R. F. (1990). Neural mechanisms of classical conditioning in mammals. *Philos Trans R Soc London Ser B* 329, 161–170.

Tsai, L.-H., Harlow, E. and Meyerson, M. (1991). Isolation of the human cdk2 gene that encodes the cyclin A- and adenovirus E1A-associated p33 kinase. *Nature* 353, 174–177.

Wang, J. H. and Feng, D. P. (1992). Postsynaptic protein kinase C essential to induction and maintenance of long-term potentiation in the hippocampal CA1 region. *Proc. Natl. Acad. Sci. USA* 89, 2576–2580.

Yen, S.-H., Kenessey, A., Lee, S. C. and Dickson, W. (1995). The distribution and biochemical properties of a cdc2-related kinase, KKIALRE, in normal and Alzheimer brains. *J. Neurochem.* 65, 2577–2584.

Yeo, C. H., Hardiman, M. J. and Glickstein, M. (1985a). Classical conditioning of the nictitating membrane response of the rabbit I. Lesions of the cerebellar nuclei. *Exp. Brain Res.* 60, 87–98.

Yeo, C. H., Hardiman, M. J. and Glickstein, M. (1985b) .1991) Classical conditioning of the nictitating membrane response of the rabbit II. Lesions of the cerebellar nuclei. *Exp. Brain Res.* 60, 99–113.

Yin, J. C. P., Wallach, J. S., Del Vacchio, M., Wilder, E. L., Zhou, H., Quinn, W. G., and Tully, T. (1994). Induction of a dominant negative CREB transgene specifically blocks long-term memory in drosophila. *Cell* 79, 49–58.

What is claimed is:

1. An isolated or purified polypeptide, said polypeptide encoded by an open reading frame in a nucleotide sequence, wherein said nucleotide sequence comprises:
   (a) nucleotide SEQ ID NO: 3;
   (b) nucleotide SEQ ID NO: 5; or
   (c) a nucleotide sequences which, as a result of the genetic code, is degenerate to the sequences of (a) or (b).

2. The polypeptide of claim 1, wherein said nucleotide sequence comprises nucleotide SEQ ID NO: 3.

3. The polypeptide of claim 1, wherein said nucleotide sequence comprises nucicotide SEQ ID NO: 5.

4. A purified or isolated polypeptide having at least 98% sequence identity to SEQ ID NO: 4.

5. The polypeptide of claim 4, wherein the polypeptide has 99.5% sequence identity to SEQ ID NO: 4.

6. The polypeptide of claim 4, wherein the polypeptide has 99.8% sequence identity to SEQ ID NO: 4.

7. The polypeptide of claim 4, wherein the polypeptide has the sequence depicted in SEQ ID NO: 4.

8. The polypeptide of claim 2, wherein the polypeptide is isolated.

9. The polypeptide of claim 2, wherein the polypeptide is purified.

10. The polypeptide of claim 3, wherein the polypeptide is isolated.

11. The polypeptide of claim 3, wherein the polypeptide is purified.

12. The polypeptide of claim 4, wherein the polypeptide is isolated.

13. The polypeptide of claim 4, wherein the polypeptide is purified.

* * * * *